United States Patent [19]

Carpino et al.

[11] Patent Number: 5,510,491
[45] Date of Patent: Apr. 23, 1996

[54] REAGENTS FOR RAPID PEPTIDE SYNTHESIS

[75] Inventors: Louis A. Carpino, Amherst, Mass.; Michael Philbin, Plainsboro, N.J.

[73] Assignee: Research Corporation Technologies, Inc., Tucson, Ariz.

[21] Appl. No.: 38,414

[22] Filed: Mar. 29, 1993

Related U.S. Application Data

[62] Division of Ser. No. 944,806, Sep. 14, 1992, Pat. No. 5,221,754, which is a continuation of Ser. No. 774,386, Oct. 11, 1991, abandoned, which is a continuation of Ser. No. 364,662, Jun. 9, 1989, abandoned.

[51] Int. Cl.⁶ .................. C07D 215/14; C07D 213/16
[52] U.S. Cl. .................. 546/344; 546/341; 546/342; 546/112; 549/53; 549/58; 568/812; 568/813
[58] Field of Search .................. 549/53, 58; 568/812, 568/813; 546/341, 342, 344, 112

[56] References Cited

U.S. PATENT DOCUMENTS

| | | | |
|---|---|---|---|
| Re. 28,496 | 7/1975 | Fancher | 260/482 |
| 3,835,175 | 9/1974 | Carpino et al. | 560/32 |
| 3,839,396 | 10/1974 | Otsuka et al. | 560/32 |
| 4,108,846 | 8/1978 | Melenhofer | 560/32 |
| 4,394,519 | 7/1983 | Carpino et al. | 560/32 |
| 4,508,657 | 4/1985 | Carpino et al. | 560/32 |
| 4,581,167 | 4/1986 | Carpino et al. | 560/32 |

*Primary Examiner*—Jacqueline Haley
*Attorney, Agent, or Firm*—Scully, Scott, Murphy & Presser

[57] ABSTRACT

This invention relates to compounds of the formula:

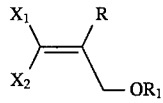

wherein R is an electron withdrawing group;

$R_1$ is H or COZ;

$X_1$ and $X_2$ are independently H, lower alkyl, aryl, aryl lower-alkyl or polystyrene or R and $X_1$ taken together with the carbon atoms to which they are attached form a ring containing from 4 to 15 ring carbon atoms and may contain up to 2 heteroatoms, wherein the heteroatoms are O, S, or N; and Z is an amino acid residue, a peptide residue or a leaving group. The compounds of the present invention are adaptable as blocking or protecting groups for an amine composition useful in peptide synthesis. The present invention is also directed to a method of protecting an amino group of an organic molecule during a reaction which modifies a portion of the molecule other than the protected amino group.

40 Claims, No Drawings

REAGENTS FOR RAPID PEPTIDE SYNTHESIS

This invention was made with Government support under RO1-GM-9076 awarded by the National Institutes of Health. The Government has certain rights in the invention.

This is a divisional of application Ser. No. 944,806, filed on Sep. 14, 1992, now U.S. Pat. No. 5,221,754, which is a File Wrapper Continuation of U.S. Ser. No. 774,386, filed on Oct. 11, 1991, now abandoned which is a File Wrapper Continuation of U.S. Ser. No. 364,662, filed on Jun. 9, 1989, now abandoned.

FILED OF THE INVENTION

This invention relates to 2-propenyl chloroformate compounds and derivatives thereof and their use in synthetic biochemistry, including peptide synthesis. More particularly, this invention relates to the use of these compounds as blocking groups which attach to primary and secondary amino groups to protect the amino group from undergoing undesirable side reactions during peptide synthesis.

BACKGROUND OF THE INVENTION

Support for the research leading to this invention was sponsored, in part, by the National Institute of Health. This support is gratefully acknowledged by the inventors.

A basic problem in peptide synthesis is one of blocking or protecting the amino group from interaction with a carboxyl group on the same amino acid. These undesirable side reactions are prevented by attaching to one amino acid a group that will render the —$NH_2$ group unreactive and still permit the desired reaction to take place. In addition to providing protection for the amino group, the blocking group is preferably one that can be easily removed without chemically altering the remainder of the molecule including the peptide linkage that has been built up during the synthesis. (See generally, Morrison and Boyd, *Organic Chemistry*, Third Ed., Sec. 30.10 Synthesis of Peptides, pp. 1131–1133 (1983).

Attempts to develop a two-support continuous solid phase technique for peptide synthesis (inverse Merrifield method) using a 9-Fluorenylmethyloxycarbonyl group (FMOC) for amino protection have been hindered due to incomplete scavenging of dibenzofulvene by the polymeric deblocking agents. These problems were partially overcome through use of the the 2-Chloro-1-indenylmethoxycarbonyl group (Climoc) for protection of amino groups (see U.S. Pat. Nos. 4,581,167 and 4,394,519 to Carpino, et al.). The present invention has devised a scheme for the development of new, Michael-addition based amino-protecting groups for which the deblocking and scavenging steps are one and the same.

The present invention is directed to compounds containing novel Michael addition based amino-protecting groups, such as 2-(t-butyl-sulfonyl)-2-propenyloxycarbonyl groups and the like. The use of the compounds of the present invention in peptide synthesis overcomes the problems resulting from ineffective scavenging occurring when the FMOC or Climoc groups are utilized as the protecting groups.

The 2-(t-Butylsulfonyl)-2-propenyloxycarbonyl group (Bspoc) and related Michael Addition-based amino-protecting groups described herein are superior for peptide synthesis. Deblocking is exceptionally rapid under mild, nonhydrolytic conditions, resulting in faster syntheses of long chain peptides with fewer side reactions, such as diketopiperazine, pyroglutamic acid and succinimide formation, thereby leading to higher yields and greater purity of the products. Due to the stability against acidic reagents, acid chlorides may be used as quick-acting coupling agents, further speeding up the process. Moreover, no significant racemization occurs in either the coupling or deblocking steps.

SUMMARY OF THE INVENTION

This invention relates to compounds for use as blocking groups to protect a primary or secondary amino group from side reactions. These compounds will be stable under acidic reaction conditions, preventing side reactions at the amino site. When protection of the amine is no longer required, these groups are rapidly removed by treatment with a nucleophile.

The compounds of this invention react readily with primary or secondary amines to form carbamates as described hereinbelow. Formation of these carbamates protects the amino group from further reaction under conditions which modify another portion of the molecule, e.g., formation of a peptide bond whereby said amino protected amino acid reacts with an unprotected amino portion of another amino acid.

Important compounds of the invention are 2-propenyloxycarbonyl compounds having the general formula 1:

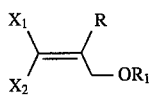

1 wherein R is an electron withdrawing group, $R_1$ is H or COZ, $X_1$ and $X_2$ are independently H, lower alkyl, aryl, aryl lower-alkyl or a solid support or R and $X_1$ taken together with the carbon atoms to which they are attached form a ring containing from 4 to 15 ring carbon atoms and may contain up to 2 heteroatoms, wherein the heteroatoms are O, S or N; and Z is a leaving group, an amino acid residue or a peptide residue.

These compounds can be derived from alcohols of the formula 2:

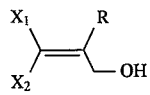

2 wherein R, $X_1$, and $X_2$ are as hereinbefore defined.

As embodied and broadly described herein, the invention also comprises a method for protecting a primary or secondary amino group of an organic molecule during a reaction which modifies a portion of the molecule other than the protected amino group.

The method comprises the steps of (a) bonding the 2-propenyloxycarbonyl compound of formula I with an amine, thereby protecting said amine from further reaction; (b) modifying a portion of the organic molecule other than the protected amine, by chemical reaction; and, (c) cleaving the protecting group from the amino group.

In a preferred embodiment, the protecting group can be rapidly and cleanly deblocked via treatment with a nucleophile. The nucleophile can also act as a scavenger for the protecting group. The preferred nucleophile is a primary or secondary amine.

DETAILED DESCRIPTION OF PREFERRED EMBODIMENTS OF THE INVENTION

Reference will now be made in detail to present preferred embodiments of the invention, examples of which are illustrated hereinbelow.

The present invention is directed to compounds of the formula 1:

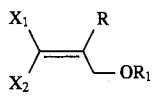

wherein R is an electron withdrawing group;

$R_1$ is H or COZ;

$X_1$ and $X_2$ are independently H, lower alkyl, aryl, aryl lower-alkyl or a solid support or R and $X_1$ taken together with the carbon atoms to which they are attached form a ring containing from 4 to 15 ring carbon atoms and may contain up to 2 heteroatoms wherein the heteroatoms are O, S or N; and Z is an amino acid residue, a peptide residue or a leaving group.

An electron withdrawing group as defined herein shall be interpreted as a group that will draw electrons to itself more than a hydrogen atom would if it occupied the same position in the molecule. See, J. March, *Advanced Organic Chemistry*, 3rd Ed., John Wiley & Sons, P.17 (1985). These types of groups are well-known to one skilled in the art.

Examples of electron withdrawing groups include $SO_2R_2$, $SOR_2$, $COOR_2$, $COR_2$, CHO, $CONR_2R_3$, CN, $CF_3$, $NO_2$, aryl, pyridyl and the like, wherein $R_2$ and $R_3$ are independently lower-alkyl having from 1 to 6 carbon atoms, aryl, aryl lower-alkyl, hetero-aryl or a solid support and the alkyl, aryl or hetero-aryl groups are unsubstituted, or mono- or di-substituted with halides, $SO_2R_2$, $SOR_2$, $COOR_2$, $COR_2$, CHO, CN, $CF_3$ or $NO_2$.

As used herein, the terms lower alkyl, when used singly or in combination, refer to alkyl groups containing one to six carbon atoms. They may be straight chain or branched and include such groups as methyl, ethyl, propyl, isopropyl, butyl, sec-butyl, isobutyl, t-butyl, pentyl, isopentyl, neopentyl, hexyl and the like. The preferred alkyl groups contain one to four carbon atoms.

The term aryl, when used alone or in combination, refer to an aromatic ring containing six to ten ring carbon atoms. The aryl group includes phenyl, and 1 or 2-naphthyl. The preferred aryl group is phenyl.

The most preferred aralkyl group is benzyl.

The term hetero-aryl when used alone or in combination refers to an hetero-aromatic ring having from four to nine carbon ring atoms and one or two hetero ring atoms. The heterocyclic rings may contain sulfur, nitrogen or oxygen. The hetero-aryl groups include quinolyl, isoquinolyl, furyl, thienyl, or pyridyl.

The preferred heteroaryl groups are 2- or 4-pyridyl.

The preferred R groups are $SO_2R_2$, $SOR_2$, $COOR_2$, $COR_2$, $CONR_2R_3$, aryl, or pyridyl, wherein $R_2$ and $R_3$ are as defined hereinabove.

Especially preferred R groups are $SO_2C(CH_3)_3$, $SOC(CH_3)_3$, $SO_2C_6H_5$, $SOC_6H_5$, 2-pyridyl, or 4-pyridyl or COOEt.

As used herein the term solid support when used singly or in combination refers to polymer resins typically used in peptide synthesis. These polymers are generally employed in the form of beads. The polymer resins preferred for peptide synthesis are polystyrenes, polyacrylamides and the like. The preferred polystyrene resin is a copolymer of styrene-divinylbenzene.

As noted hereinabove, R and $X_1$ taken together with the carbons to which they are attached may be cyclic containing one, two, or three rings. Said cyclic structure may contain from four to fifteen ring carbon atoms and up to two heteroatoms. These heterocyclic ring atoms may be sulfur, oxygen or nitrogen. For example, when R and $X_1$ taken together form a ring, the compound of the present invention may have the formula 3 or its isomer 3a:

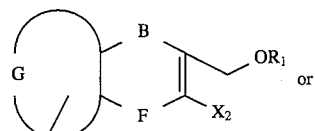

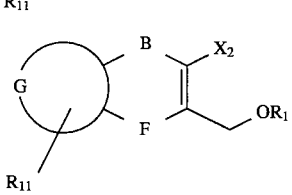

wherein B is a chemical bond, $CR_8R_9$ $$\overset{O}{\underset{||}{C}},$$

$SO_2$, SO, RP(O), or S, R is lower alkyl or $OR_{10}$, $R_{10}$ is lower alkyl, $R_8$, $R_9$, $R_{12}$ and $R_{13}$ are independently hydrogen or lower alkyl, G is a mono or bicyclic fused ring system containing 5 to 10 carbon atoms and may contain up to 2 heteroatoms, F is a chemical bond, $CR_{12}R_{13}$, $SO_2$, SO, RP(O) or S, $R_{11}$ is hydrogen or lower alkyl and $X_2$ and $R_1$ are as defined hereinabove. G may be completely saturated, partially unsaturated or fully aromatic (e.g. a benzo system). Examples of G include cyclopentyl, cyclohexyl, cyclopentenyl, cyclohexenyl, decalinyl, phenyl, naphthyl, pyridyl azaindenyl and the like.

As defined hereinabove, when F is a chemical bond, then 3 or 3a has the structure

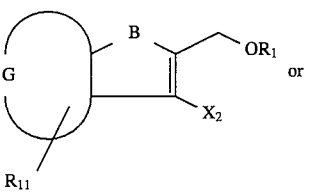

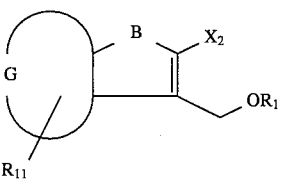

Similarly, when B is a chemical bond, then 3 or 3a has the structure

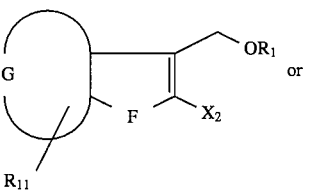

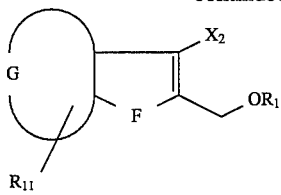

However, in order to be effective, either B or F is an electron withdrawing group or ring G is itself electron withdrawing. In other words, if ring G is heterocyclic, i.e., contains ring heteroatoms, then B and F are independently any of the values described hereinabove. However, if ring G is not heterocyclic (e.g., is aromatic or cycloalkyl), then at least one of B or F is

$SO_2$, SO, RP(O)
or S wherein R is as defined hereinabove.

A preferred class of 3 or 3a has the formula

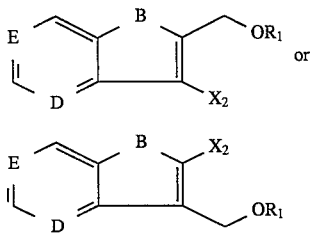

wherein B is $CR_8R_9$ or $SO_2$ and E and D are independently CH or N, provided that when B is $CR_8R_9$, then E or D is N.

A preferred embodiment has the formula 4:

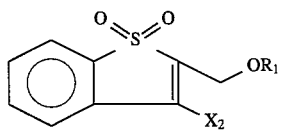

or the formula 4a or 4b:

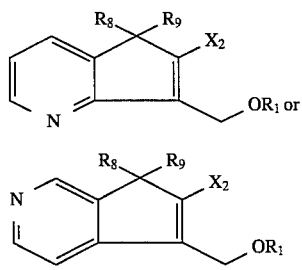

wherein $X_2$ and $R_1$ are as defined hereinabove and $R_8$ and $R_9$ are independent.

When compounds of the present invention are used to protect a primary or secondary amino group and introduce the 2-propenyloxy carbamate compound of Formula I, Z is a leaving group. As is generally known in the art and for the purposes of the present invention "a leaving group" is defined as a group which is readily broken away from its union with the carbon atoms. It is one which readily joins, for example, with an active hydrogen atom to split out a compound containing the hydrogen atom and the leaving group. Leaving groups are generally electron attracting groups either because of their electronegativity or because they have an inductive effect. Leaving groups are defined in U.S. Pat. No. 4,394,519 to Carpino, et al. which is incorporated herein by reference.

The preferred leaving groups Z are halo, CN, $SR_4$, SAr, $N_3$, OAr,

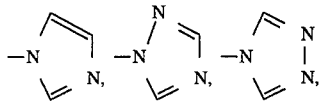

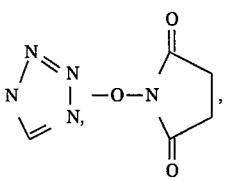

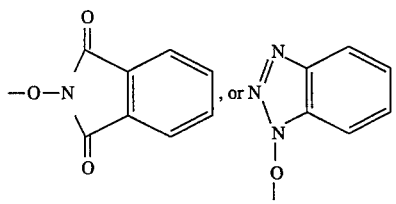

wherein $R_4$ is lower-alkyl, aryl or aryl lower-alkyl, wherein the alkyl or aryl groups are unsubstituted, or mono- or di-substituted with halides, $SO_2R_4$, $SOR_4$, $COOR_4$, $COR_4$, CHO, CN, $CF_3$ or $NO_2$.

The most preferred leaving groups are halo, especially Cl and Br.

When Z is an amino acid residue or a peptide residue it becomes part of a stable system. An amino acid residue as defined herein as an amino acid or derivative thereof, such as an ester and the like, minus an amine hydrogen on the amino end of the molecule. A peptide residue is a peptide of two or more amino acids or derivatives thereof, such as an ester and the like, linked through an amide bond and it contains one less amino hydrogen on the amino end of the peptide.

In a preferred embodiment Z is an alpha-amino acid.

The alpha-amino acids are those which are well known to one skilled in the art. These amino acids, e.g., the naturally occurring alpha-amino acids, are often used in the chemical synthesis of peptides. These amino acids include alanine, arginine, asparagine, aspartic acid, cysteine, cystine, glutamic acid, glutamine, glycine, histidine, hydroxylysine, hydroxyproline, isoleucine, leucine, lysine, methionine, phenylalanine, proline, serine, threonine, tryptophan, tyrosine, valine, penicillamine, and the like.

The preferred groups in the vinyl position, $X_1$ and $X_2$, are independently H, phenyl, lower alkyl having from 1 to 4 carbon atoms or a solid support. Especially preferred groups for $X_1$ and $X_2$ are independently H or phenyl. The $X_1$ and $X_2$ positions may also be used as the site of attachment to a polymer resin, on Z, when, Z is an amino acid or peptide residue.

The preferred compounds of the invention have the formula 1:

wherein R is $SO_2R_2$, $SOR_2$, $COOR_2$, $CONR_2R_3$, aryl or 2- or 4-pyridyl, wherein $R_2$ and $R_3$ are as defined hereinabove or R and $X_1$ taken together with the carbon atoms to which they are attached form a ring, the ring having from 4 to 15 ring carbon atoms and up to a total of 3 rings, often forming a fused benzo-system; $R_1$ is H or COZ and Z is halo or an amino acid; and $X_1$ and $X_2$ are independently H, phenyl or lower alkyl.

The preferred groups in compounds wherein R and $X_1$ are taken together with the carbon atoms to which they are attached are $SO_2C_6H_4$ or $C_5H_3NCH_2$ thereby describing compounds of the formula 4 or 4a or 4b described hereinabove:

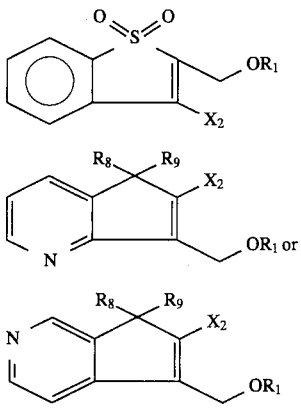

wherein $R_1$ and $X_2$, $R_8$ and $R_9$ are as defined hereinabove, and $R_8$ and $R_9$ are independently hydrogen or lower alkyl.

The most preferred compounds of the invention are the 2-propenyloxy chloroformates wherein R is $SO_2C(CH_3)_3$, $SOC(CH_3)_3$, $SO_2C_6H_6$, $SOC_6H_6$, COOEt, 2-pyridyl or 4-pyridyl; Z is Cl or Br; and $X_1$ and $X_2$ are H or phenyl.

The preferred alcohols of the present invention are:
2-(t-butylsulfonyl)-2-propenyl alcohol,
2-carboethoxy-2-propenyl alcohol,
2-(phenylsulfonyl)-2-propenyl alcohol,
(E)-3-phenyl-2-(phenylsulfonyl)-2-propenyl alcohol,
(Z)-3-phenyl-2-(phenylsulfonyl)-2-propenyl alcohol,
3,3-diphenyl-2-(phenylsulfonyl)-2-propenyl alcohol,
Benzothiophenesulfone-2-methanol,
3,3-dimethyl-2-(phenylsulfonyl)-2-propenyl alcohol.

The preferred chloroformates of the present invention are:
2-(t-butylsulfonyl)-2-propenyl chloroformate,
2-carboethoxy-2-propenyl chloroformate,
2-(phenylsulfonyl)-2-propenyl chloroformate,
(E)-3-phenyl-2-(phenylsulfonyl)-2-propenyl chloroformate,
(Z)-3-phenyl-2-(phenylsulfonyl)-2-propenyl chloroformate, or
3,3-diphenyl-2-(phenylsulfonyl)-2-propenyl chloroformate,
Benzothiophenesulfone-2-methyl chloroformate,
3,3-dimethyl-2-(phenylsulfonyl)-2-propenylchloroformate.

The 2-propenyloxy carbonyl compounds outlined hereinabove can be formed by art-recognized techniques known to one skilled in the art. Exemplary procedures are outlined hereinbelow.

The compounds of the present invention having the formula 1a: can be prepared from the corresponding alcohol 2:

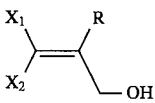

as illustrated in the following equations:

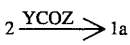

wherein $Z=Y=Cl$, Br, F/, CN; $Z=Cl$, $Y=SR_4$, SAr, OAr, F/;

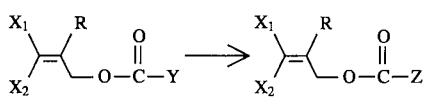

wherein Z=Cl, Br; Y=F, $N_3$, CN.

In the above equations, $X_1$, $X_2$, R, and $R_4$ are as defined herein.

Typically, reactions such as indicated by Equation (1) are carried out in an inert organic solvent. As defined herein an inert solvent is a reaction inert solvent, i.e., one which will not react with the reagents or reactants under the given reaction conditions. Suitable solvents are halogenated or non-halogenated hydrocarbons containing up to about eight carbon atoms, e.g., methylene chloride, ethylene dichloride, benzene, isooctane and the like. Reactions are conducted at temperatures of from about 0° C. to about 25° C. during a reaction period of from about 1 to about 6 hours. Suitable yields are obtained with equimolar quantities of reactants, although the yield may often be appreciably increased by utilizing an excess of either one of them, for example, up to about a 20% molar excess. Generally speaking, the halogen substituted compounds are prepared under less rigorous reaction conditions than are required for the preparation of those compounds wherein the substituent is of higher molecular weight. The presence of a weak base, may increase the rate of reaction.

Reactions of Equation (2) in which the substituent placed on the carbonyl carbon atom is initially present in an ionic form are carried out in inert polar organic solvents which will enhance ionization, including, for example, acetonitrile, dimethylformamide, dimethylsulfoxide, tetrahydrofuran, dioxane and the like. The reaction is normally carried out at a temperature of from about 0° C. to about 25° C. during a period of from about 1 to 5 hours. Preferably equimolar quantities of reactants are employed to minimize side reactions but a moderate excess of either reactant would not introduce appreciable difficulties.

Compounds of Formula 2 can be prepared by reacting an aldehyde or ketone of Formula 5:

with a Wittig reagent, $\varnothing_3PCHR$,

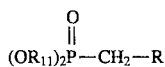

or $(R_{11})_3SiCH_2-R$ such as,

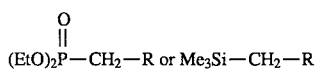

where R is defined hereinabove, and $R_{11}$ is lower alkyl under Wittig reaction conditions; followed by the addition of formaldehyde under Prins reaction conditions, wherein $X_1$, $X_2$ and R are as hereinbefore described and $R_{11}$ is lower alkyl.

The compounds of the present invention wherein R contains a sulfur atom can be prepared by an alternative route. The following procedures as depicted in Scheme I is illustrative for the preparation of these compounds:

Scheme I

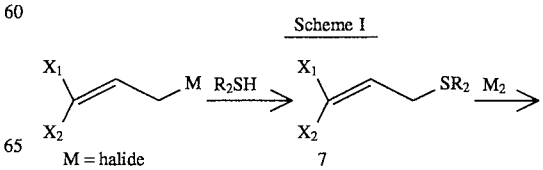

M = halide

-continued
Scheme I

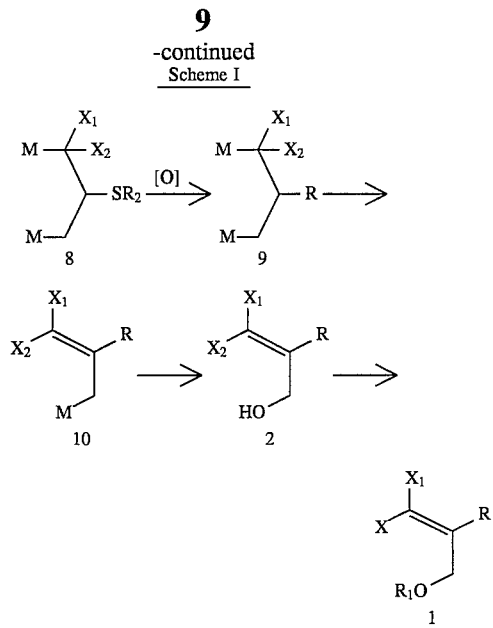

An allylic halide such as allyl bromide (6), is treated with a thiol, $R_2SH$, such as t-butylthiol in strong base to form the corresponding thioether 7. Halogenation of the thioether forms the dihalo thioether 8 which in turn is oxidized with an oxidizing agent to form the sulfonyl or sulfinyl compound 9. Various oxidizing agents can be used to effect said reaction, such as MCPBA. Compound 9 is then reacted with a strong base, such as lutidine, to form the corresponding unsaturated compound 10. Substitution of the halide in compound 10 with hydroxide forms the compound of Formula 2. The compound of Formula 1 can be readily prepared from 2 according to the procedure described hereinabove.

Typically, the reactions for synthesis of the compounds described in Scheme 1 hereinabove are carried out in an inert organic solvent. Suitable solvents include alcohols, such as methanol, ethanol, isopropanol, t-butanol and the like, ethers such as diethyl ether, 1,4-dioxane, tetrahydrofuran (THF) and the like, hydrocarbons, such as benzene, hexane, cyclohexane, toluene, Skelly solvents and the like, and halogenated hydrocarbons such as $CHCl_3$, $CCl_4$, $CH_2Cl_2$ and the like.

Temperatures for these reactions range from about −78° C. to the reflux temperature of the solvent being employed. Unless indicated to the contrary in the discussion of the various reaction schemes described hereinabve and hereinafter, the preferred temperatures are from about 0° C. to about 100° C.

The compounds described hereinabove can be used to protect primary and secondary amines. In fact, an embodiment of the present invention is directed to the method for protecting a primary or secondary amino group on an organic molecule during a reaction which modifies a portion of the molecule other than the protected amino group, comprising the steps of:

a) reacting the amine with a compound of the formula:

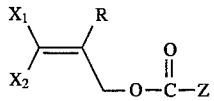

wherein

Z is a leaving group;

$X_1$ and $X_2$ are independently H, lower alkyl, aryl, aryl lower-alkyl or a solid support;

R is an electron withdrawing group; or

R and $X_1$ with the carbon atoms to which they are attached form a ring containing from 4 to 15 ring carbon atoms and up to two heteroatoms selected from the group consisting of nitrogen, sulfur or oxygen;

b) modifying a portion of the molecule other than the protected amine, by chemical reaction; and c) removing the protecting group from the amino group.

The reagents described hereinabove are useful in protecting primary or secondary amino groups during synthesis of organic molecules including bioorganic molecules, e.g., peptides and polypeptides, nucleotides and polynucleotides.

An application of the present invention is using the compounds described herein wherein Z is a leaving group to protect the amino group in an amino acid during peptide synthesis. Therefore, the present invention is also directed to the method for the preparation of a peptide which comprises:

a) reacting an amino acid having a free amino group with a compound of the formula:

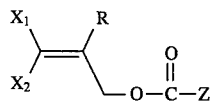

wherein

Z is a leaving group;

$X_1$ and $X_2$ are independently H, lower alkyl, aryl, aryl lower-alkyl or a solid support;

R is an electron withdrawing group; or

R and $X_1$ with the carbon atoms to which they are attached form a ring containing from 4 to 15 ring carbon atoms;

b) reacting the product of (a) with an amino acid or peptide having a free amino group; and c) removing the protecting group.

Thus in the most preferred embodiment, compounds of the present invention can be used as blocking groups for amino acids during peptide synthesis. The preferred amino acids are alpha-amino acids.

More specifically, the compounds of Formula 1a, wherein Z is a leaving group, can react with a carboxyprotected amino acid as indicated hereinbelow in Scheme II:

Scheme II

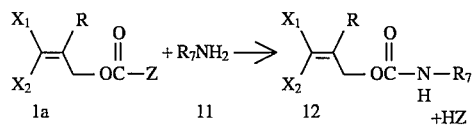

In the above scheme, $X_1$, $X_2$, R, Z are as defined above, and $R_7NH_2$ (11) is an alkyl or aryl amine or an alpha-amino acid. Examples of the amines are aniline, p-chloroaniline and the like. The alpha-amino acids are the alpha-amino acids described herein above and include phenylalanine, glycine, valine, and the like. Often the amino acids are protected by a carboxy protecting group known in the art.

A variety of carboxy protecting groups known in the art may be employed. Examples of many of these possible groups may be found in "Protective Groups in Organic Synthesis" by T. W. Green, John Wiley and Sons, 1981. The preferred carboxy protecting group is the t-butyl ester.

In the above scheme, a compound of Formula 1a is reacted with a carboxy protected amino acid to form 12 which is then hydrolyzed in acid to form a compound of Formula 1 wherein Z is an amino acid adduct.

The most preferred protecting group are Bspoc; i.e., 2-(t-butylsulfonyl)-2-propenyloxycarbonyl and Bsmoc, i.e., Benzothiophenesulfone-2-methyloxycarbonyl.

If the leaving group is a halogen, especially chlorine, the reaction may be effected in an inert, polar organic solvent such as dioxane, tetrahydrofuran, dimethylformamide, pyridine or other solvent containing, for example, up to eight carbon atoms. The reaction is run under alkaline conditions, typically dilute aqueous alkali metal base such as sodium or potassium hydroxide or carbonate, at low temperatures, for example, from about 0° C. to 25° C. during a period of from about 2 to 3 hours. Usually the protected amino acid or peptide will precipitate upon acidification of the mixture, and may be purified by any appropriate method such as recrystallization. Excess blocking reagent may be employed, even up to 0.5 molar excess, but equimolar quantities of reactants generally give better results.

The protected amines can also be prepared by reaction of the 2-propenyl alcohols with isocyanates. This reaction will form a 2-propenyl carbamate directly without requiring the conversion of the alcohols to chloroformate.

PREPARATION OF PEPTIDES

The 2-propenyloxy carbonyl group, once placed on the amino function to be protected is especially stable. This makes it possible to use a variety of methods for forming peptides without danger of cleavage of the protecting group. In fact, the group is stable under acidic conditions, such as using hydrogen bromide or chloride in various organic solvents, or trifluoroacetic acid, involved in the removal of most of the commonly used protecting groups. This is a special advantage of the particular compounds of this invention; their use greatly increases the options available to the skilled peptide chemist for the preparation of complex polypeptides.

For coupling an N-protected amino acid or peptide of this invention with a free amino group of another amino acid or peptide to produce di-, tri-, and higher oligopeptides, any of a wide variety of procedures are available. Generally speaking, most of the coupling procedures normally employed by the skilled practitioner can be used. For example, a carboxy protected amino acid can be reacted with an amino-protected amino acid under peptide forming conditions, i.e., amide forming conditions, in the presence of a coupling agent, such as dicyclohexylcarbodiimide (DCC). In this way, amino acids can be added to the chain sequentially until the desired peptide is synthesized.

The use of activated esters, suitable aryloxy or thioaryl esters, especially substituted phenyl esters such as p-nitrophenyl or pentafluorophenyl esters, also leads to satisfactory results. In fact, most of the procedures used for the placement of the 2-propenyloxycarbonyl function for the protection of an amino group can be used for the coupling reaction.

One coupling procedure which is especially favored is to convert the free carboxy end of the 2-propenyloxycarbonyl protected amino acid or peptide into an N-hydroxy succimimide or 1-hydroxybenzotriazole (HOBt) ester. This may be accomplished using dicyclohexylcarbodiimide. The ester is coupled with the amino group under alkaline conditions in an inert, polar, organic solvent such as dimethylformamide, an ester, ether or alcohol containing up to about six carbon atoms. Any mild alkaline reagent such as alkali metal hydroxides, carbonates or bicarbonates, or alkali metal salts of lower aliphatic carboxylic acids can be employed. If the amino acid or peptide to be coupled is in the form of an ester, sodium acetate in water is the preferred alkaline reagent. If it is in the form of a free acid, sodium hydroxide is the preferred reagent. The reaction takes place at from about 15° C. to about 30° C. during a period of from about 10 to 50 hours. It is generally most economical to use a slight molar excess, e.g., up to about 20% molar excess of one of the reactants, although equimolar quantities can also be employed.

It will be apparent, also, that in the course of the synthesis, it may be necessary to protect certain groups to prevent unwanted side reactions. For example, it may be necessary to protect the hydroxyl group of tyrosine, a delta or gamma carboxyl group of aspartic or glutamic acid, or the epsilon amino group of lysine so as to prevent interference by these groups in the main desired reaction. This is a common problem in peptide synthesis and many procedures are available for dealing with it. Such procedures are known to the skilled peptide chemist. (See for example, "Reagents for Organic Synthesis", by T. W. Green, John Wiley and Sons 1981.)

Any of the usual groups employed for protecting or blocking carboxyl groups in peptide chemistry can be employed in this instance. The principal criteria for selection of such groups, as is well known to the skilled artisan is that they should be easily placed on, stable to the reaction condition, and easily removed. Generally, the most preferred procedure is to form esters according to procedures known to one skilled in the art, and this is the preferred procedure for this reaction. The preferred esters are alkyl or alkaryl groups containing up to eight carbon atoms such as methyl, ethyl, tert-butyl, phenyl, benzyl, or p-methylbenzyl.

CLEAVAGE OF THE PROTECTING GROUP

As mentioned above, a special advantage of the particular novel compounds of this invention as blocking agents for amino acids and peptides is that they can be cleaved under mild conditions. Another feature is that the conditions of cleavage can be varied, depending upon the $X_1$ and $X_2$ substituents on the 2-propenyloxycarbonyl group. Thus, it is possible to remove other protecting groups present, e.g., acid protecting groups, under a variety of conditions specifically without affecting the 2-propenyloxycarbonyl groups which may be present in the molecule. For example, these other protecting groups can be cleaved under acidic conditions without cleaving the protecing groups of the present invention.

The 2-propenyl carbamate protecting groups of the present invention are readily cleaved by treatment of the protected amine (2-propenyl carbamate) with a nucleophile. For the purpose of this disclosure, a nucleophile is an electron-rich atom, i.e., an atom which can donate an electron pair, which tends to attack a carbon nucleus but does not act as a Bronsted Lowry base . The nucleophile as defined herein is a nucleophile which is used for nucleophilic addition across a double bond and behaves in a manner similar to that described in Schemes III and IV herein below.

The general mechanism for cleavage of the 2-propenyl carbamates to provide the free amine is believed to be a Michael-type addition to a double bond, as shown in scheme III:

Scheme III

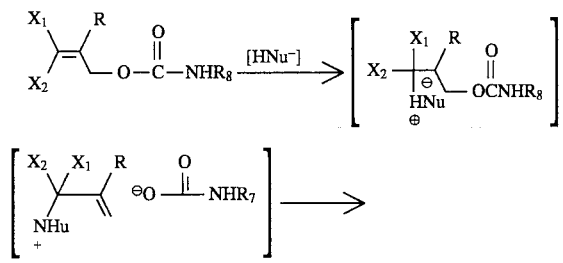

-continued
Scheme III

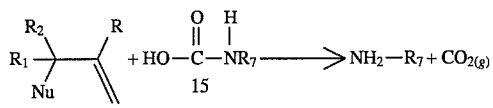

The nucleophile is believed to attack at the terminal carbon atom of the propenyl group (Michael acceptor) forming a zwitterion which can eliminate the $OCNR_7$ anion and $H^+$ to form an alkene-amine and the amide (15) after protonation. Rearrangement and loss of $CO_2$ will furnish the free amine 11.

The nucleophiles which will function in concert with this invention must have an active hydrogen atom, i.e., a hydrogen atom attached to the nucleophilic atom.

It is preferred that the nucleophile is a simple amine. It is especially preferred that the simple amine is a primary or secondary of the formula $HNR_5R_6$ wherein $R_5$ and $R_6$ are independently hydrogen, lower alkyl or substituted lower alkyl, the lower alkyl being substituted with OH, $CH_3$, or $CH_2CH_3$ or $R_5$ and $R_6$ taken together form a mono or bicyclic ring containing from 4 to 10 ring carbon atoms and 1 or 2 heteroatoms selected from the group consisting of nitrogen, sulfur or oxygen.

Typical examples of useful amines include ethanolamine, morpholine, piperidine, diethylamine, 2,6-dimethylpiperidine, piperazine, diethyl amine and ethylamine and the like.

An organo mercaptan can also be used as a nucleophile, e.g., alkyl mercaptans, cycloalkyl mercaptans, aryl mercaptan or aralkyl mercaptans. The most preferred mercaptan is benzyl mercaptan.

The nucleophile can be added as a free compound or as an insoluble reagent attached to a solid support i.e., polystyrene or silica dioxide. These are represented by the formula:

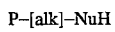

wherein P is an organic polymer as defined hereinabove or a polymer having the formula $[SiO_2]n$; alk is a chemical bond, alkyl or aroyl chain having from about one to about ten carbon atoms and Nu-H is a nucleophile as defined hereinabove.

A preferred insoluble reagent in the silica based piperizine reagent 17:

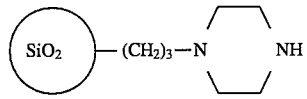

Another useful nucleophile is benzylmercaptan as shown in Scheme IV.

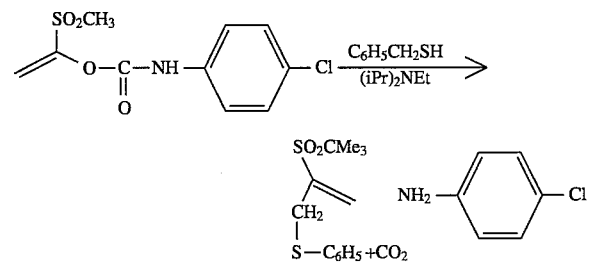

In this scheme the thio-group reacts in a Michael fashion to remove the Bspoc protecting group.

The enormous reactivity of the 2-propenyloxy carbonyl group might lead one to expect an insuperable problem as far as synthetic applications are concerned since even amino acid esters can effect deblocking. However, this is not the case. As shown by the clean conversion of the chloroformates to protected carbamates, the carbonyl group is much more electrophilic than the double bond so that competing attack at the latter does not occur. Similarly no difficulties are experienced during coupling of Bspoc amino acids with amino acid esters during the formation of peptide bonds.

Even the DCC method for peptide synthesis is successful, although the best results are achieved using the acid chlorides. HPLC and GC analysis showed that these coupling reactions occurred without significant racemization (<0.1%) of the amino acids.

Deblocking of the Bspoc function by means of the insoluble silica-based piperazine reagent 17 is also exceptionally rapid and leads to 100% scavenging of the Bspoc

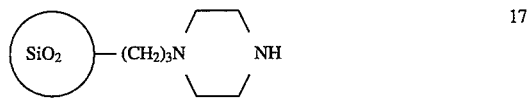

fragment. Such rapid and clean reactions promise general applicability for the use of 2-propenyloxy carbonyl (Michael-based systems) protecting groups in two-support, inverse Merrifield solid phase peptide synthesis. The inverse Merrifield solid phase synthesis is described in U.S. Pat. No. 4,623,484, incorporated herein by reference.

Typical reaction apparatus useful for solid phase peptide synthesis (SPPS) are polypropylene vials or flasks which can be subjected to vortex mixing or shaking. These flasks are often equipped with a fritted glass filter to remove excess liquid solvents and reagents by using pressure or suction filtration. Use of these types of flasks will minimize handling of the solid support(s).

Other apparatus useful for SPPS are columns packed with solid supports. Solid supports which function in SPPS are disclosed hereinabove. There are two methods in general use which employ columns. One, the Merrifield method, employs the solid support for attachment of the amino acid or peptide residues. This method employs N-protected amino acids as building blocks which are added to an amino acid or peptide residue attached to the solid support at the carbonyl (acid) end of the molecule. After the peptide bond has been formed, the protecting group is removed and the cycle repeated. When a peptide having the desired sequence has been synthesized, it is then removed from the support.

The second method, inverse Merrifield, employs reagents attached to solid supports in a series of columns. The amino acid or peptide residue is passed through these columns in series to form the desired amino acid sequence. (See U.S. Pat. No. 4,623,484).

Michael-based systems as described herein can be controlled by the use of substituents at the vinyl-positions in addition to manipulation of the nature of the electron-withdrawing group (EWG). Thus the presence of one or two substituents on $X_1$ and $X_2$ in compounds of Formula 1a should serve to slow down

the deprotecting process, should it be necessary to protect against any tendency toward premature deprotection (avoidance of side reactions). Such derivatives are also expected to be more stable in solvents, such as DMF, in which certain of the unsubstituted 2-propenyloxy carbamates may not be usable due to slow degradation. Additional selectivity is possible via the use of hindered deblocking agents, e.g., methylated piperidines. The relative rate of deblocking various protecting groups of the present invention are indicated Tables I, II, and III hereinbelow.

TABLE I

Relative Rates of Deprotecting for $$\text{R-C(=CH}_2\text{)-CH}_2\text{-OCONHR}_2 \quad / \quad \text{2,6-dimethylpiperidine}$$

| R | Time for Complete Reaction, hrs. |
|---|---|
| —COOEt | 2.8 |
| —SOC$_6$H$_5$ | incomplete after 7 days |
| —SO$_2$CMe$_3$ | 0.8 |
| —SO$_2$C$_6$H$_5$ | 0.4 |

TABLE II

Relative Rates for Deprotecting for
SO$_2$CMe$_3$ $$\text{OCONHR}_7\text{/B}$$

| B | Time for Complete Reaction, hrs. |
|---|---|
| piperidine (NH) | instantaneous |
| 2,6-dimethylpiperidine | 0.8 |
| 2,2,6,6-tetramethylpiperidine | incomplete after 72 hours |

TABLE III

Relative Rates for Deprotecting for $$X_1\text{-C(SO}_2R_2\text{)=C(X}_2\text{)-CH}_2\text{-OCONHR}_7/ \text{ piperidine}$$

| R | X$_1$ | X$_2$ | Time for Complete Reaction, min. |
|---|---|---|---|
| phenyl | H | phenyl | 38 |
| phenyl | phenyl | H | 20 |
| phenyl | phenyl | phenyl | stable after 3 days |
| phenyl | H | H | instantaneous |

It should be noted that in addition to their applicability to inverse Merrifield synthesis, the various Michael-based protecting groups described herein can be used in classical Merrifield solid phase peptide synthesis in place of FMOC protection. In such cases the use of Bspoc amino acid chlorides, pentafluorophenyl or HOBt esters or the BOP reagent allow rapid coupling reactions. Increased solubility of all key reagents is observed. Additional advantages of such a substitution include drastic lowering of the time required to assemble a long peptide chains and lessening of side reactions. These groups can also be substituted for base-sensitive functions (FMOC, etc.) in ordinary solution synthesis, both single-step and repetitive, and as protectants for DNA coupling reactions.

EXAMPLES

The invention will now be illustrated by examples. The examples are not intended to be limiting of the scope of the present invention. In conjunction with the general and detailed description above, the examples provide further understanding of the present invention and outlines a synthesis of a preferred embodiment of the invention.

The following examples represent preferred embodiments of the compositions of the invention and methods for carrying out the blocking and deblocking of amides as can be applied to peptide and polypeptide synthesis. The starting materials for the examples whose method of preparation are not indicated, are commercially available compounds which would be available from chemical supply houses well known to the art such as Aldrich Chemical Co.

EXAMPLE 1 t-Butyl Allyl Sulfide. To a solution of 350 mL of anhydrous ethanol maintained under nitrogen was slowly added 22.99 g (1 mol) of sodium spheres. The sodium dissolved within 90 minutes, and to the resulting sodium ethoxide solution was added 90.19 g (1 mol) of t-butyl mercaptan with mechanical stirring. Allyl bromide (120.98 g; 1 mol) was then added dropwise to the mechanically stirred sodium t-butyl thiolate solution. After the addition was complete, the mixture was refluxed for 10 minutes, the solution allowed to cool, the precipitated sodium bromide filtered, and the ethanol removed by distillation at atmospheric pressure. The residue was diluted with 200 mL of water, and the layers separated. The aqueous layer was extracted with five 40-mL portions of ether. The combined organic layers were extracted with 150 mL of water, the organic layer dried over MgSO$_4$, filtered, and the solvent removed in vacuo from a water bath at 45° C. to give a yellow liquid. Distillation through a 0.8×15-cm fractionating column gave 56.16 g (45%) of the sulfide as a colorless liquid, bp 139–°141° C.; IR (neat), cm$^{-1}$ 3090, 2960 1635, 1455, 1360, 1160, 985, 915; $^1$H NMR (CDCl$_3$) 1.35 (s, 9H, t-butyl), 3.20 (d, 2H, CH$_2$), 4.90–6.25 (m 3H, vinyl).

EXAMPLE 2

1,3-Dibromo-2-(t-butylsulfonyl) Propane. To a stirred solution of 17.37 g (0.13 mol) of t-butyl allyl sulfide in 133 mL of CCl$_4$ at −24° C. (CCl$_4$/dry ice) was added dropwise a solution of 21.33 g (0.13 mol) of Br$_2$ in 67 mL of CCl$_4$. A yellow solid precipitated during the addition. The mixture was warmed to room temperature and stirred for 10 minutes following complete solution of the yellow solid. The resulting solution was poured into a mixture of 55.50 g (0.27 mol) of 85% m-chloroperbenzoic acid in 490 mL of CH$_2$Cl$_2$ kept at −24° C., and the mixture stirred for 30 minutes at this temperature. The cooling bath was then removed and the mixture stirred at room temperature overnight. The precipitated m-chlorobenzoic acid was filtered and the filtrate washed with three 200-mL portions of saturated NaHCO$_3$, followed by 200 mL of water. The organic layer was dried over MgSO$_4$, filtered, and the solvent removed in vacuo from a water bath at 45° C. The crude product was recrystallized from 20% EtOAc/Skelly B to give 32.02 g (75%) of the dibromide, mp 139–°140° C.; IR (KBr), cm$^{-1}$ 2980, 1470, 1365, 1285, 1105, 860, 840, 685; $^1$NMR (CDCl$_3$) 1.45 (S, 9H, t-butyl), 3.80–4.00 (m, 5H, CH and CH$_2$).

EXAMPLE 3

2-(t-Butylsulfonyl)-2-propenyl Bromide. A mixture of 16.78 g (0.052 mmol) of 1,3-dibromo-2-(t-butylsulfonyl) propane and 14 mL (0.12 mol) of 2,6-lutidine in 55 mL of $CH_2Cl_2$ was refluxed for 75 minutes. The solution was allowed to cool to room temperature and extracted with three 80-mL portions of 5% HCl followed by 80 mL of water. The organic layer was dried over $MgSO_4$, filtered, and the solvent removed in vacuo from a water bath at 45° C. to give 11.46 g (91%) of the allyl bromide as a white solid, mp 40.5–°42.0° C., which was used without further purification; IR (KBr) 2980 cm$^{-1}$, 1480, 1395, 1230, 1100, 970, 730, 640; $^1$H NMR (CDCl$_3$)δ 1.40 (s, 9H, t-butyl), 4.30 (s, 2H $CH_2Br$), 6.50 (s, 2H, vinyl).

EXAMPLE 4

2-(t-Butylsulfonyl-2-propenyl Alcohol. A mixture of 8.55 g (35.3 mmol) of 2-(t-butylsulfonyl)-2-propenyl bromide and 5.31 g (78.1 retool) of sodium formate in 150 mL of methanol was refluxed overnight. The solution was allowed to cool and concentrated to 50 mL with the aid of a water aspirator, resulting in the precipitation of excess sodium formate. The residue was diluted with 150 mL of water and extracted with five 50-mL portions of $CH_2Cl_2$. The organic layer was dried over $MgSO_4$, filtered, and the solvent removed in vacuo from a water bath at 45° C. The crude product was recrystallized from 15% EtOAc/Skelly F to give 4.30 g (68%) of the alcohol as a colorless solid, mp 53.5–°54.5° C.; IR (KBr), cm 3470, 3120, 3000, 1450, 1370, 1270, 1095, 1050, 960, 900, 800, 750, 630; $^1$H NMR (CDCl$_3$)δ 1.39 (s, 9H, t-butyl), 2.57 (t, 1H, OH), 4.56 (d, 2H $CH_2O$), 6.30 (s, 1H, vinyl), 6.31 (s, 1H, vinyl).

Anal. Calcd for $C_7H_{14}O_3S$: C, 47.17; H, 7.92; S. 17.99. Found: C, 47.07; H, 7.95; S, 17.70.

EXAMPLE 5

2-(t-Butylsulfonyl)-2-propenyl Chloroformate. To a solution of 6.67 g (37.4 mmol) of 2-(t-butylsulfonyl)-2-propenyl alcohol in 27 mL of dry THF at 0° C. was added in one portion 27 mL of phosgene. The solution was stirred for 1 hour at 0° C. and allowed to stand at room temperature overnight. Excess phosgene and solvent were removed under reduced pressure. The crude product was recrystallized from 25% ether/Skelly B to give 8.23 g (91%) of the chloroformate as a colorless solid, mp 56.5–57.7; IR (KBr) cm$^{-1}$ 2980, 1755, 1430, 1380, 1290, 1140, 1100, 965, 915, 810, 750, 680, 630; $^1$H NMR (CDCl$_3$) δ 1.41 (s, 9H, t-butyl), 5.11 (s, 2H, $CH_2O$), 6.37 (s, 1H, vinyl), 6.47 (s, 1H, vinyl).

Anal. Calcd for $C_8H_{13}ClO_4S$: C, 39.92; H, 5.44; S, 3.32. Found: C, 40.10; H, 5.40; S, 13.07.

EXAMPLE 6

2-(t-Butylsulfonyl)-2-propenyl N-p-Chlorophenyl Carbamate. To a solution of 0.24 g (1.0 mmol) of 2-(t-butylsulfonyl)-2-propenyl chloroformate in 3 mL of benzene at 0° C. was added dropwise 0.26 g (2.0 mmol) of p-chloroaniline 3 mL of benzene. A white precipitate separated almost immediately. After the addition was complete the mixture was stirred at 0° C. for 10 minutes and for 2 hours at room temperature. The mixture was then diluted with 15 mL of benzene and extracted with two 15-mL portions of 5% HCl, followed by 15 mL of water. The organic layer was dried over $MgSO_4$, filtered, and the solvent removed in vacuo from a water bath at 45° C. The crude product was recrystallized from 20% EtOAc/Skelly B to give 0.26 g (79%) of the urethane, mp 124–°125° C. The same compound was obtained in 85% yield by treatment of 2-(t-butylsulfonyl)- 2-propenyl alcohol with p-chlorophenyl isocyanate in refluxing benzene; IR (KBr) cm$^{-1}$ 3340, 3120, 2980, 1730, 1600, 1490, 1430, 1280, 1210, 1070, 975, 915, 830, 750, 620; $^1$H NMR (CDCl$_3$) δ 1.4 (s, 9H, t-butyl), 4.0 (t, J=1 Hz, 2H, $CH_2O$), 6.3 (s, 1H, vinyl), 6.35 (s, 1H, vinyl), 7.15–7.5 (m, 5H, phenyl and NH).

Anal. Calcd. for $C_{14}H_{18}ClNO_4S$: C, 50.68; H, 5.47; N, 4.22. Found: C, 50.46; H, 5.47; N, 4.28.

EXAMPLE 7

2-Phenylthio-2-propenyl Alcohol. To a stirred solution of 36.0 g (0.64 mol) of propargyl alcohol and 0.12 g (1.8 mmol) of powdered potassium hydroxide, was added dropwise at 125° C. over 30 minutes, 60.0 g (0.54 mol) of thiophenol. The mixture was stirred for an additional 90 minutes, and allowed to cool to room temperature. The brown solution was diluted with 200 mL of ether, and extracted with three 100-mL portions of 2N sodium hydroxide, and two 100-mL portions of water. The organic phase was dried over $MgSO_4$, filtered, and the solvent removed in vacuo from a water bath at 45° C. to give 90.4 g of a brown liquid, which, according to NMR analysis, contained 34% of the desired isomer. The mixture was fractionally distilled through a 0.8×20-cm column packed with glass helices to give 29.5 g of a colorless liquid, which by NMR analysis contained 67% of the desired isomer, bp 109–°116° C./1.2 Torr. This liquid was chromatographed on silica gel (100–200 mesh, 50 g/gram of compound) with 20% EtOAc/Skelly B as eluant, to give 16.4 g (18%) of the sulfide as a colorless liquid; IR (neat) cm$^{-1}$ 3360, 1610, 1580, 1470, 1430, 1040, 740, 690; $^1$H NMR (CDCl$_3$) δ 3.70 (t, 1H, OH), 4.10 (d, 2H, $CH_2$), 5.2 (t, J=1 Hz, 1H, vinyl), 5.55 (t, J=1 Hz, 1H, vinyl), 7.15–7.55 (m, 5H, phenyl).

EXAMPLE 8

2-(Phenylsulfonyl)-2-propenyl Alcohol. A mixture of 5.03 g (30.3 mmol) of 2-(phenylthio)-2-propenyl alcohol and 12.74 g (62.7 mmol) of 85% m-chloroperbenzoic acid in 250 mL of $CH_2Cl_2$ was stirred overnight at room temperature. The mixture was extracted with three 100-mL portions of saturated $NaHCO_3$, followed by 100 mL of water. The organic layer was dried over $MgSO_4$, filtered, and the solvent removed in vacuo from a water bath at 45° C. The residue was chromatographed on silica gel (100–200 mesh, 50 g/gram of compound) with 40% EtOAc/Skelly B as eluant, to give 4.30 g (72%) of the sulfone as a colorless oil; IR (neat) cm$^1$ 3500, 1580, 1440, 1300, 1170, 1130, 1050, 950, 900, 750, 690; $^1$H NMR (CDCl$_3$) δ 3.70 (bs, 1H, OH), 4.20 (bs, 2H, $CH_2$) 6.05 (bs, 1H, vinyl), 6.35 (bs, 1H, vinyl) 7.30–7.95 (m, 5H, phenyl).

Anal. Calcd for $C_9H_{10}O_3S$: C, 54.53; H, 5.08; S. 16.17. Found: C, 54.57; H, 5.13; S, 16.02.

EXAMPLE 9

2-(Phenyl sulfonyl)-2-propenyl N-p-Chlorophenyl Carbamate. A solution of 3.38 g (17.1 mmol) of 2-(phenylsulfonyl)-2-propenyl alcohol and 2.62 g (17.1 mmol) of p-chlorophenyl isocyanate in 15 mL of benzene was refluxed overnight. The solvent was removed in vacuo from a water bath at 45° C. to give a solid which was recrystallized twice from $CCl_4$ to give 4.25 g (71%) of the urethane, mp 104°–106° C.; IR (KBr) cm$^{-1}$ 3320, 1730, 1600, 1530, 1300, 1215, 1065, 960, 820, 750, 680; $^1$H NMR (CDCl$_3$) δ 4.85 (bs, 2H, $CH_2$), 6.16 (bs, 1H, vinyl), 6.50 (bs, 1H, vinyl), 7.05–8.00 (m, 10H, phenyl and NH).

Anal. Calcd for $C_{16}H_{14}ClNO_4S$: C, 54.63; H, 4.01; N, 3.98. Found: C, 54.54; H, 3.99; N, 4.05.

EXAMPLE 10

2-(Methylsulfonyl)ethyl N-p-Chlorophenyl Carbamate.

A solution of 2.06 g (16.6 mmol) of 2-(methylsulfonyl)ethyl alcohol and 2.55 g (16.6 mmol) of [-chlorophenyl isocyanate in 15 mL of benzene was refluxed for 30 minutes. The solvent was removed in vacuo from a water bath at 45° C. to give a solid which was recrystallized from $CHCl_3$ to give 2.98 g (65%) of the urethane, mp 147°–147.5° C.; IR (KBr) 3360 $cm^{-1}$, 1720, 1600, 1490, 1310, 1230, 1130, 1070, 830, 760; $1^1H$ NMR (DMSO-$d_6$-$CDCl_3$) δ 3.0 (s, 3H, $CH_3$), 3.40 (t, 2H, $CH_2SO_2$), 4.60 (t, 2H, $CH_2O$), 7.15–7.55 (m, 4H, phenyl), 9.20 (bs, 1H, NH).

Anal. Calcd for $C_{10}H_{12}ClNO_4S$: C, 43.25; H, 4.36; N, 5.04. Found: C, 43.16; H, 4.14; N, 4.99.

EXAMPLE 11

2-Carboethoxy-2-propenyl Alcohol. To a stirred solution of 12.07 g (53.8 mmol) of triethyl phosphonacetate and 21 mL of 35–40% aqueous formaldehyde at room temperature was added dropwise a solution of 13.2 g (95.5 mmol) of $K_2CO_3$ in 50 mL of water. The temperature of the reaction mixture rose to 48° C. over the course of the addition. After the addition was complete, the mixture was stirred for 1 hour, quenched with 22 mL of saturated $NH_4Cl$ solution, and extracted with three 25-mL portions of ether. The organic layer was dried over $Na_2SO_4$, filtered, and the solvent removed in vacuo from a water bath at 45° C. to give a colorless liquid which was distilled to give 4.57 g (65%) of the colorless alcohol, bp 60°–65° C./0.9 Torr; IR (neat) $cm^{-1}$ 3450, 1710, 1635, 1450, 1400, 1300, 1260, 1160, 1050, 945, 820; $^1H$ NMR ($CDCl_3$) δ 1.30 (t, 3H, $CH_3$), 3.5–4.5 (m, 5H, $CH_2OH$ and $CO_2CH_2$), 5.90 (bs, 1H, vinyl), 6.25 (bs, 1H, vinyl).

EXAMPLE 12

2-Carboethoxy-2-propenyl N-p-Chlorophenyl Carbamate. A solution of 2.12 g (16.3 mmol) of 2-(carbo-ethoxy)-2-propenyl alcohol and 2.50 g (16.3 mmol) of p-chlorophenyl isocyanate in 15 mL of benzene was refluxed overnight. The solvent was removed in vacuo from a water bath at 45° C. to give a solid which was recrystallized from $CCl_4$ to give 2.99 g (65%) of the urethane, mp 93.0–°93.5° C.; IR (KBr) $cm^{-1}$ 3360, 1720, 1600, 1525, 1390, 1310, 1220, 1170, 1060; $^1$NMR (DMSO-$d_6$/$CDCl_3$) δ 1.25 (t, 3H, $CH_3$), 4.25 (q, 2H, $CO_2CH_2$), 4.90 (s, 2H, $CH_2O$), 5.90 (bs, 1H, vinyl), 6.35 (bs, 1H, vinyl), 7.15–7.50 (m, 4H, phenyl), 8.0 (bs, 1H, NH).

Anal. Calcd. for $C_{13}H_{14}ClNO_4$: C, 55.04; H, 4.97; N, 4.94. Found: C, 54.89; H, 4.69; N, 4.89.

EXAMPLE 13

2-(Phenylsulfinyl)-2,propenyl Alcohol. To a stirred solution of 0.91 g (5.5 mmol) of 2-(phenylthio)-2-propenyl alcohol in 60 mL of $CH_2Cl_2$ at −78° C. was added 1.11 g (5.5 mmol) of 85% m-chloroperbenzoic acid. The reaction mixture was stirred for 1 hour at −78° C. The cooling bath was removed and the mixture allowed to warm to room temperature. The mixture was filtered, and then extracted with three 50-mL portions of saturated $NaHCO_3$. The organic layer was dried over $MgSO_4$, filtered, and the solvent removed in vacuo from a water bath at 45° C. The residue was flash chromatographed on silica gel (230–400 mesh, 4×12-cm packed column) with 80% EtOAc/Skelly B as eluant, to give 0.57 g (57%) of the sulfoxide as a colorless oil; IR (neat) $cm^{-1}$ 3360, 1440, 1030, 990, 930, 750, 690; $^1H$ NMR ($CDCl_3$) δ 4.00 (s, 1H, allylic), 4.15 (s, 1H, allylic), 4.40 (bs, 1H, OH), 5.90 (t, J=1 Hz, 1H, vinyl), 6.05 (s, 1H, vinyl), 7.35–7.80 (m, 5H, phenyl).

EXAMPLE 14

2-(Phenylsulfinyl)-2-propenyl N-p-Chlorophenyl Carbamate. A solution of 0.57 g (3.1 mmol) of 2- (phenylsulfinyl)- 2-propenyl alcohol and 0.48 g (3.1 mmol) of p-chlorophenyl isocyanate in 10 mL of benzene was refluxed overnight. The solvent was removed in vacuo from a water bath at 45° C. to give a brown oil which was recrystallized from $CCl_4$/Skelly B to give 0.72 g (69%) of the urethane, mp 106–°107.5° C.; IR (KBr) $cm^{-1}$ 3240, 1730, 1600, 1545, 1490, 1310, 1220, 1030, 745, 680; $^1H$ NMR ($CDCl_3$) δ 4.65 (s, 1 H, allylic), 4.70 (s, 1H, allylic), 6.00 (s, 1H, vinyl), 6.30 (s, 1H, vinyl), 7.10–7.85 (m, 10H, phenyl and NH).

Anal. Calcd for $C_{16}H_{14}ClNO_3S$: C, 57.23; H, 4.20; N, 4.17. Found: C, 56.95; H, 4.14; N, 4.10.

EXAMPLE 15 t-Butyl 2-(t-Butylsulfonyl)-2-propenyoxcarbonyl-L-phenylalaninate. To a stirred solution of 0.185 g (0.768 mmol) of 2-(t-butylsulfonyl)-2-propenyl chloroformate in 2 mL of benzene at 0° C. was added dropwise a solution of 0.34 g (1.53 mmol) of t-butyl L-phenylalaninate in 5 mL of benzene. Upon addition, a white precipitate began to separate. Upon completion of the addition, the slurry was stirred at room temperature for 30 minutes, poured into 15 mL of ether and washed with three 15-mL portions of 5% HCl, and 15 Ml of water. The organic layer was dried over $MgSO_4$, filtered, and the solvent removed in vacuo from a water bath at 45° C. The resulting oil was recrystallized from 20% ether/pentane to give 0.23 g (70%) of the colorless ester, mp 67–°69° C.; IR (KBr) $cm^{-1}$ 3410, 2980, 1715, 1510, 1365, 1290, 1155, 1095, 1060, 940, 750, 700, 625; $^1H$ NMR ($CDCl_3$) δ 1.45 (s, 9H, t-butyl), 1.50 (s, 9H, t-butyl), 3.12 (m, 2H, benzyl), 4.56 (q, 1H, CH), 4.90 (s, 2H, $CH_2O$), 5.38 (d, 1H, NH), 6.14 (s, 1H, vinyl), 6.29 (s, 1H, vinyl), 7.15–7.40 (m, 5H, Phenyl); $[α]_D^{28}$+25.4° (c=1, $CH_2Cl_2$), also, $[α]_{546}^{28}$ +30.9° (c=1, $CH_2Cl_2$).

Anal. Calcd for $C_{21}H_{31}NO_6S$: C, 59.27; H, 7.34; N, 3.29. Found: C, 59.31; H, 7.45; N, 3.23.

EXAMPLE 16

Methyl 2-(t-Butylsulfonyl)-2-propenyloxycarbonyl-L-phenylalaninate. A mixture of 0.507 g (2.11 mmol) of 2-(t-butylsulfonyl)- 2-propenyl chloroformate and 0.454 g (2.11 mmol) of methyl L-phenylalaninate hydrochloride in 15 mL of $CH_2Cl_2$ was stirred in the presence of 25 mL of 5% $NaHCO_3$ at room temperature for 4.25 hours. The aqueous phase was separated, and the organic phase was washed with two 30-mL portions of 5% HCl. The organic phase was dried over $MgSO_4$, filtered, and the solvent removed in vacuo from a water bath at 45° C. The crude product was recrystallized from 20% EtOAc/Skelly F to give 0.61 g (75%) of the methyl ester, mp 63–°64° C.; IR (KBr) $cm^{-1}$ 3390, 1755, 1715, 1515, 1290, 1225, 1100, 1065, 945, 750, 700; $^1H$ NMR ($CDCl_3$) δ 1.39 (s, 9H, t-butyl), 3.13, (m, 2H, benzyl), 3.75 (s, 3H, $OCH_3$), 4.68 (q, 1H, CH), 4.88 (s, 2H, $CH_2O$), 5.32 (d, 1H, NH), 6.11, (s, 1H, vinyl), 6.26 (s, 1H, vinyl), 7.10–7.40 (m, 5H, phenyl); 1 $[α]_D^2$+33.3° (c=1, $CHCl_3$), also $[α]_{546}^{23}$+40.4° (c=1, $CHCl_3$).

Anal. Calcd for $C_{18}H_{25}NO_6S$: C, 56.38; H, 6.57; N, 3.65. Found: C, 56.68; H, 6.24; N, 3.64.

EXAMPLE 17

2-(t-Butylsulfonyl)-2-propenylcarbonyl-L-phenylalanine. A solution of 4.57 g (19.0 mmol) of 2-(t-butylsulfonyl)- 2-propenyl chloroformate and 5.64 g (18.6 mmol)

of 1-butyl L-phenylalaninate hydrophosphite in 90 mL of $CH_2Cl_2$ was stirred in the presence of 165 mL of 5% $NaHCO_3$ at room temperature for 2 hours. The aqueous phase was separated, and the organic phase washed with three 75-mL portions of 5% HCl. The organic phase was dried over $MgSO_4$, filtered, and the solvent removed in vacuo from a water bath at 45° C. The resulting oil was dissolved in 36 mL of 50% $CH_2Cl_2$/triflouroacetic acid, and the solution stirred at room temperature for (91%) of the colorless acid, mp 88.0–°89.5° C.; IR (KBr) $cm^{-1}$ 3270, 1760 1690, 1520, 1290, 1200, 1100, 1060, 960, 755, 700, 630; $^1H$ NMR ($CDCl_3$) 1.40 (s, 9H, t-butyl), 3.20 (m, 2H, benzyl), 4.75 (q, 1H, CH), 4.90 (s, 2H, $CH_2O$), 5.35 (d, 1H, NH), 6.15 (s, 1H, vinyl), 6.32 (s, 1H, vinyl), 7.15–7.40 (m, 5H, phenyl); $[\alpha]_D^{24}$ −31.0° (c=0.5, DMF), also $[\alpha]_{546}^{24}$ −37.5° (c=0.5 DMF).

Anal. Calcd for $C_{17}H_{23}NO_6S$: C, 55.27; H, 6.27; N, 3.79. Found: C, 55.02; H, 6.47; N, 3.71.

EXAMPLE 18

2-(t-Butylsulfonyl)-2-propenyloxycarbonyl-L-phenylalanyl Chloride. To a stirred solution of 2.50 g (6.77 mmol) of 2- (t-butylsulfonyl) -2-propenyloxycarbonyl-L-phenylalanine in 15 mL of dry $CH_2Cl_2$, was added dropwise under a nitrogen atmosphere, a solution of 4.9 mL (10 eq) of thionyl chloride in 10 mL of dry $CH_2Cl_2$. Upon completion of the addition, the solution was refluxed for 2 hours. The solution was cooled to room temperature, and excess thionyl chloride and solvent were removed under reduced pressure with the aid of a vacuum pump. The crude residue was recrystallized from 30 mL of 33% $CH_2Cl_2$/pentane to give 2.13 g (82%) of the acid chloride, mp 100.0–°100.5° C.; IR (KBr) $cm^{-1}$ 3400, 1810, 1790, 1720, 1510, 1295, 1250, 1105, 760, 710, 630; $^1H$ NMR ($CDCl_3$) δ 1.38 (s, 9H, t-butyl), 3.27 (m, 2H, benzyl), 4.88 (m, 3H, $CH_2O$ and CH), 5.27 (d, 1H, NH), 6.10 (s, 1H, vinyl), 6.27 (s, 1H, vinyl), 7.15–7.45 (m, 5H, phenyl); $[\alpha]_{546}^{26}$+15.3° (c=1, $CH_2Cl_2$) also $[\alpha]_D^{26}$ +18.7° (c=1, $CH_2Cl_2$).

Anal. Calcd for $C_{17}H_{22}ClNO_5S$: C, 52.64; H, 5.72; N, 3.61. Found: C 52.32; H, 5.39; N, 3.55.

EXAMPLE 19

2- (t-Butylsulfonyl)-2-propenyloxycarbonyl Glycine.

A mixture of 3.34 g (13.9 mmol) of 2-(t-butylsulfonyl)-2-propenyl chloroformate and 2.95 g (13.8 mmol) of t-butyl glycinate hydrophosphite in 85 mL of $CH_2Cl_2$ was stirred in the presence of 100 mL of 5% $NaHCO_3$ at room temperature for 4 hours. The aqueous phase was separated, and the organic phase washed with three 33-mL portions of 5% HCl. The organic phase was dried over $MgSO_4$, filtered, and the solvent removed in vacuo from a water bath at 45° C. The resulting oil was dissolved in 20 mL of 50% $CH_2Cl_2$/triflouroacetic acid, and the solution stirred at room temperature for 2 hours. Excess triflouroacetic acid and solvent were removed in vacuo from a water bath at 45° C. The resulting oil was recrystallized from 30% EtOAc/Skelly B to give 3.25 g (84%) of the acid, mp 105.0–°105.5° C.; IR (KBr) $cm^{-1}$ 3355, 1765, 1695, 1560, 1290, 1190, 1100, 1050, 770; $^1HNMR$ ($CDCl_3$) δ 1.41 (s, 9H, t-butyl), 4.05 (d, 2H, $CH_2$), 4.94 (s, 2H, $CH_2O$), 5.44 (t, 1H, NH), 6.26 (s, 1H, vinyl), 6.33 (s, 1H, vinyl).

Anal. Calcd for $C_{10}H_{17}NO_6S$: C, 43.00; H, 6.13; N, 5.01. Found: C, 43.00; H, 6.03; N, 4.97.

EXAMPLE 20

2-(t-Butylsulfonyl)-2-propenyloxycarbonyl Glycyl Chloride. To a stirred mixture of 0.404 g (1.45 mmol) of 2-(t-butylsulfonyl)-2-propenyloxycarbonyl glycine in 4 mL of dry $CH_2Cl_2$, was added dropwise under a nitrogen atmosphere, a solution of 1.06 mL (10 eq) of thionyl chloride in 4 mL of dry $CH_2Cl_2$. Upon completion of the addition, the solution was refluxed for 1 hour. The solution was cooled to room temperature, and excess thionyl chloride and solvent were removed under reduced pressure with the aid of a vacuum pump. The crude product was recrystallized from $CH_2Cl_2$/pentane to give 0.39 g (91%) of the acid chloride, mp 61.5–°62.5° C.; IR (KBr) $cm^{-1}$ 3400, 1800, 1740, 1510, 1280, 1100, 1050, 945, 790, 750, 625; $^1H$ NMR ($CDCl_3$) δ 1.41 (s, 9H, t-butyl), 4.39 (d, 2H, $CH_2$), 4.95 (s, 2H, $CH_2O$), 5.57 (bs, 1H, NH), 6.25 (s, 1H, vinyl), 6.35 (s, 1H, vinyl).

Anal. Calcd for $C_{10}H_{16}ClNO_5S$: C, 40.34; H, 5.42; N, 4.70. Found: C, 40.51; H, 5.30; N, 4.83.

EXAMPLE 21

2-(t-Butylsulfonyl)-2-propenyloxycarbonyl-D-valine.

A solution of 1.01 g (4.15 mmol) of 2-(t-butylsulfonyl)-2-propenyl chloroformate and 0.87 g (4.15 retool) of t-butyl D-valinate hydrochloride in 22 mL of $CH_2Cl_2$ was stirred in the presence of 45 mL of saturated $NaHCO_3$ for 90 minutes. The aqueous phase was separated, and the organic phase was washed with two 20-mL portions of 5% HCl. The organic phase was dried over $MgSO_4$, filtered, and the solvent removed in vacuo from a water bath at 45° C. The resulting oil was dissolved in 10 mL of 50% $CH_2Cl_2$/trifluoroacetic acid, and the solution stirred at room temperature for 90 minutes. Excess triflouroacetic acid and solvent were removed in vacuo from a water bat. h at 45° C. The resulting oil was recrystallized from ether/Skelly F to give 1.01. g (75%) of the colorless acid, mp 113–°114° C.; IR (KBr) $cm^{-1}$ 3380, 3160, 1750, 1700, 1540, 1400, 1295, 1100, 1025, 760, 665; $^1H$ NMR ($CDCl_3$) δ 0.9 (d, 3H, $CH_3$), 1.05 (d, 3H, $CH_3$), 1.4 (s, 9H, t-butyl), 2.2 (m, 1H, CH), 4.3 (d of d, 1H, CHN), 4.95 (s, 2H, $CH_2O$), 5.5 (d, 1H, NH), 6.25 (s, 1H, vinyl), 6.35 (s, 1H, vinyl), 11.6 (s, 1H, $CO_2H$); $[\alpha]_D^{25}$ +3.2° (c=1, $CHCl_3$), also $[\alpha]_{546}^{25}$+3.7° (c=1, $CHCl_3$).

Anal. Calcd for $C_{13}H_{23}NO_6S$: C, 48.58; H, 7.21; N, 4.36. Found: C, 48.70; H, 6.99; N, 4.29.

EXAMPLE 22

Methyl 2-(t-Butylsulfonyl)-2-propenyloxycarbonyl-L-phenyalanyl-L-leucinate. A solution of 1.042 g (2.69 mmol) of 2-(t-butyl-sulfonyl-2-propenyloxycarbonyl-L-phenylalanyl chloride and 0.488 g (2.69 mmol) of methyl L-leucinate hydrochloride in 40 mL of $CH_2Cl_2$ was stirred with 60 mL of saturated $NaHCO_3$ at room temperature for 45 minutes. The aqueous layer was separated, and the organic layer washed with two 40-mL portions of 5% HCl. The organic layer was dried over $MgSO_4$, filtered, and the solvent removed in vacuo from a water bath at 45° C. The residue was recrystallized from 20% EtOAc/Skelly F to give 1.07 g (80%) of the colorless dipeptide, mp 58–°60° C.; IR (KBr) $cm^{-1}$ 3320, 2980, 1740, 1660, 1540, 1300, 1110, 1060, 750, 700; $^1H$ NMR ($CDCl_3$) δ 0.91–1.70 H (m, 18H, aliphatic), 3.12 (d, 2H, benzyl), 3.73 (s, 3H, $OCH_3$), 4.43 (q, 1H, CH), 4.59 (q, 1H, CH), 4.89 (s, 2H, $CH_2O$), 5.46 (d, 1H, NH), 6.10 (m, 2H, vinyl and NH), 6.28 (s, 1H, vinyl), 7.18–7.40 (m, 5H, phenyl); $[\alpha]_D^{28}$ −7.1° (c=3, $CHCl_3$), also $[\alpha]_{546}^{28}$ −8.0° (c=3, $CHCl_3$).

Anal. Calcd for $C_{24}H_{36}N_2O_7S$: C, 58.04; H, 7.31; N, 5.64. Found: C, 58.02; H, 7.27; N, 5.62.

EXAMPLE 23 t-Buty 2-(t-Butylsulfonyl)-2-propenyloxycarbonyl-L-phenylalanyl-L-phenylalaninate. A solution of 0.564 g (1.45 mmol) of 2-(t-butylsulfonyl)-2-propenyloxycarbonyl-L- phenylalanyl chloride and 0.441 g (1.45 mmol) of t-butyl phenylalaninate hydrophosphite in 25 mL of $CH_2Cl_2$ was stirred with 30 mL of saturated $NaHCO_3$ at room temperature for 1 hour. The aqueous phase was separated, and the organic layer washed with two 40-mL portions of 5% HCl. The organic layer was dried over $MgSO_4$, filtered, and the solvent removed in vacuo from a water bath at 45° C. The residue was recrystallized from 20% EtOAc/Skelly B to give 0.64 g (77%) of the colorless dipeptide, mp 129.0–°130.0° C.; IR (KBr) $cm^{-1}$ 3300, 1730, 1655, 1530, 1295, 1150, 1100, 750, 700; $^1$H NMR δ 1.40 (s, 18H, t-butyl), 3.07 (m, 4H, benzyl), 4.40 (q, 1H, CH), 4.67 (q, 1H, CH), 4.88 (s, 2H, $CH_2O$), 5.35 (d, 1H, NH), 6.06 (s, 1H, vinyl), 6.18 (d, 1H, NH), 6.26 (s, 1H, vinyl), 7.17–7.35 (m, 10H, phenyl); $[\alpha]_D^{29}$ +27.5° (c=1, $CHCl_3$), also $[\alpha]_{546}^{29}$ +33.6° (c=1, $CHCl_3$).

Anal. Calcd for $C_{30}H_{40}N_2O_7S$: C, 62.92; H, 7.04; N, 4.89. Found: C, 62.94; H, 7.02; N, 4.89.

EXAMPLE 24

Benzyl 2-(t-Butylsulfonyl)-2-propenyloxycarbonyl-L-phenylalanyl-L-leucinate. A solution of 0.773 g (1.99 mmol) of 2-(t-butylsulfonyl)-2-propenyloxycarbonyl-L-phenylalanyl chloride and 0.761 g (1.93 mmol) of benzyl L-leucinate hydrotosylate in 20 mL of $CH_2Cl_2$ was stirred in the presence of 50 mL of saturated $NaHCO_3$ for 20 minutes. The aqueous phase was separated, and the organic phase washed with two 25-mL portions of 5% HCl. The organic phase was dried over $MgSO_4$, filtered, and the solvent removed in vacuo from a water bath at 45° C. The residue was recrystallized from 30% EtOAc/Skelly F to give 0.80 g (73%) of the colorless dipeptide, mp 44–°46° C.; IR (KBr) $cm^{-1}$ 3320, 1735, 1660, 1530, 1300, 1110, 1055, 750, 700; $^1$H NMR ($CDCl_3$) δ 0.9–2.1 (m 18H, aliphatic), 3.05 (d, 2H, benzyl), 4.2–4.7 (m, 2H, CH), 4.9 (s, 2H, $CH_2O$), 5.15 (s, 2H, benzyl), 5.6 (d, 1H, NH), 6.1 (s, 1H, vinyl), 6.35 (m, 2H, NH, and vinyl), 7.25 (s, 5H, phenyl), 7.35 (s, 5H, phenyl); $[\alpha]_D^{28}$ –10.4 (c=1, $CHCl_3$), also $[\alpha]_{546}^{28}$ –11.7° (c=1, $CHCl_3$).

Anal. Calcd for $C_{30}H_{40}N_2O_7S$: C, 62.92; H, 7.04; N, 4.89. Found: C, 62.81; H, 6.92; N, 4.86.

EXAMPLE 25 t-Butyl 2-(t-Butylsulfonyl)-2-propenyloxycarbonyl-L-phenylalanyl glycinate. A solution of 0.697 g (1.80 mmol) of 2-(t-butylsulfonyl)-2-propenyloxycarbonyl-L-phenylalanyl chloride and 0.371 g (1.74 mmol) of t-butyl glycinate hydrophosphite in 25 mL of $CH_2Cl_2$ was stirred in the presence of 40 mL of saturated $NaHCO_3$ for 25 minutes. The aqueous phase was separated, and the organic phase was washed with two 40-mL portions of 5% HCl. The organic phase was dried over $MgSO_4$, filtered, and the solvent removed in vacuo from a water bath at 45° C. The residue was recrystallized from EtOAc/Skelly B to give 0.54 g(64%) of the dipeptide, mp 86.5–°87.5° C.; IR (KBr) $cm^{-1}$ 3380, 1750, 1660, 1530, 1300, 1170, 1105, 955, 750, 710, 630; $^1$H NMR ($CDCl_3$) δ 1.35 (s, 9H, t-butyl), 1.45 (s, 9H, t-butyl), 3.1 (m, 2H, benzyl), 3.9 (d, 2H, $CH_2$), 4.45 (q, 1H, CH), 4.85 (s, 2H, $CH_2O$), 5.7 (d, 1H, NH), 6.05 (s, 1H, vinyl), 6.35 (s, 1H, vinyl), 6.5 (m, 1H, NH), 7.25 (s, 5H, phenyl); $[\alpha]_D^{26}$ –4.8°(c=1, $CHCl_3$), also $[\alpha]_{546}^{26}$ –5.9° (c=1, $CHCL_3$).

Anal. Calcd for $C_{23}H_{34}N_2O_7S$: C, 57.24; H, 7.10; N, 5.80. Found: C, 57.42; H, 6.99; N, 6.16.

EXAMPLE 26 t-Butyl 2-(t-Butylsulfonyl)-2-propenyloxycarbonyl-L-phenylalanyl-L-phenylalanyl-L-phenylalaninate. To a stirred solution of 3.45 g (3.45 mmol) of aminomethylpiperidnyl silica gel in 10 mL of $CH_2Cl_2$ was added 197 mg (0.344 mmol) of t-butyl 2-(t-butylsulfonyl)-2-propenyloxycarbonyl-L-phenylalanyl-L-phenylalaninate. The mixture was stirred for 20 minutes, filtered, and the silica washed with two 10-mL portions of $CH_2Cl_2$. To this $CH_2Cl_2$ solution was added 138 mg (0.345 mmol) of 2-(t-butylsulfonyl)-2-propenyloxycarbonyl-L-phenylalanyl chloride, followed by 40 mL of saturated $NaHCO_3$. The reaction mixture was stirred at room temperature for 20 minutes. The phases were separated, the organic layer was extracted with two 20-mL portions of saturated $NaHCO_3$, two 20-mL portions of 5% HCl, dried over $MgSO_4$, filtered, and the solvent removed in vacuo from a water bath at 45° C. Recrystallization from 20% EtOAc/Skelly B gave 187 mg (75%) of the tripeptide, mp 97.0–°99.0° C.; IR (KBr) $cm^{-1}$ 3300, 2980, 1730, 1660, 1540, 1300, 1160, 1110, 1060, 760, 710; $^1$H NMR ($CDCl_3$) 1.33 (s, 18H, t-butyl), 3.00 (d, 6H, benzyl), 4.33–4.85 (m, 5H, $CH_2O$ and CH), 5.50–6.75 (m, 5H, NH and vinyl), 7 23 (bs, 15H, phenyl); $[\alpha]_D^{25}$ +8.1° (c=0.6, $CHCl_3$), also $[\alpha]_{546}^{25}$ +11.2° (c=0.6, $CHCl_3$).

Anal. Calcd for $C_{39}H_{49}O_8N_3S$: C, 65.07; H, 6.86; N, 5.84. Found: C, 64.99; H, 6.84; N, 5.86.

EXAMPLE 27 trans-Phenyl β-Styryl Sulfide. To a stirred solution of 14.0 g (0.137 mol) of freshly distilled phenylacetylene at 0° C. was added dropwise 15.1 g (0.137 mol) of thiophenol. The solution was stirred at room temperature overnight. The reaction mixture was distilled to give 22.2 g (76%) of a colorless liquid, bp 177–°181° C./5 Torr. NMR analysis showed a trans/cis-ratio of 80/20. $^1$H NMR ($CDCl_3$)δ 6.53 (d, J=1, Hz, 1H, cis-vinyl), 6.81 (d, J=2 Hz 1H, trans-vinyl).

EXAMPLE 28 trans-Phenyl β-Styryl Sulfone. To a slightly frozen mixture of 8.17 g (38.5 mmol) of an 80/20 trans-cis-mixture of phenyl β-styryl sulfide in 160 mL of acetic acid was added dropwise 16 mL of 30% hydrogen peroxide. The solution was refluxed for 1 hour, poured on crushed ice to give an oil which soon solidified, and was filtered. The crude solid was dissolved in 100 mL of $CH_2Cl_2$, dried over $MgSO_4$, filtered, and the solvent removed in vacuo from a water bath at 45° C. to give 6.64 g (71%) of a solid which contained approximately 15% of the cis-isomer as determined by $^1$H-NMR analysis. Recrystallization from 30% EtOAc/Skelly B gave 3.2 g (34%) of the pure colorless sulfone, mp 72.5–°73.5° C.; $^1$H NMR ($CDCl_3$) 6.8 (d, J=15 Hz; 1H, vinyl), 7.2–8.1(m, 11H, vinyl and phenyl).

EXAMPLE 29

(E)-3-Phenyl-2-(phenylsulfonyl)-2-propenyl Alcohol. To a stirred solution of 2.0 g (8.2 mmol) of trans-phenyl β-styryl sulfone in 50 mL of dry THF at –78° C. was added dropwise under a nitrogen atmosphere 6.0 mL (8.4 mmol) of 1.4 M n-BuLi within 5 minutes. The reddish-purple solution was stirred at –78° C. for 30 minutes. Gaseous formaldehyde, generated by heating paraformaldehyde at 170° C., was passed through a 5-mm tube into the reaction mixture with the aid of a slow stream of nitrogen at –78° C. for 45 minutes. The mixture was allowed to come to room temperature over a period of 30 minutes while continuing to pass formaldehyde through the reaction mixture until a pale yellow solution was obtained. The reaction was quenched with 75 mL of 5% HCl and extracted with 50 mL of ether. The organic layer was washed with two 50-mL portions of water, dried over $MgSO_4$, filtered, and the solvent removed in vacuo from a water bath at 45° C. to give 2.1 g (93%) of the crude alcohol as a brown oil. The oil was flash chromatographed in two 1.05 g batches on silica gel (230–400 mesh, 4×19-cm column) with 50% ether/Skelly B as eluant to give 0.99 g (44%) of a light yellow solid, mp 85–°87° C. Recrystallization from 40% ether/Skelly B gave the pure colorless alcohol, mp 88–°89° C.; IR (KBr) cm$^{-1}$ 3470, 1625, 1445, 1285, 1145, 1020, 770, 755, 735, 700, 680; $^1$H NMR (CDCl$_3$) δ 2.63 (t, 1H, OH), 4.37 (d, 2H, CH$_2$O), 7.27–8.13 (m, 11H, phenyl and vinyl).

Anal Calcd for C$_{15}$H$_{14}$O$_3$S: C 65.67; H 5 14; S 11.69. Found: C, 65.60; H, 5.12; S, 11.31.

EXAMPLE 30

(E) -3-Phenyl-2-(phenylsulfonyl)-2-propenyl N-p-Chlorophenyl Carbamate. A solution of 0.56 (2.04 mmol) of (E)-3-phenyl-2-(phenylsulfonyl)-2-propenyl alcohol and 0.32 g (2.08 mmol) of p-chlorophenyl isocyanate in 10 mL of benzene was refluxed for 120 hours. The solvent was removed in vacuo from a water bath at 45° C. The crude solid was recrystallized from 20% EtOAc/Skelly B to give 0.41 g (47%) of the colorless urethane, mp 138.5–°139.5° C.; IR (KBr) cm$^{-1}$ 3320, 1695, 1590, 1520, 1305, 1230, 1150, 1045; $^1$H NMR (CDCl$_3$)δ 5.07 (s, 2H, CH$_2$O), 6.52 (bs, 1H, NH), 7.25–8.08 (m, 14H, phenyl), 8.15 (s, 1H, vinyl).

Anal. Calcd for C$_{22}$H$_{18}$ClNO$_4$S: C, 61.75; tt, 4.24; N, 3.27. Found: C, 61.54; H, 4.27; N, 3.11.

EXAMPLE 31

Thiophenyl Trimethylsilyl Methane. To a stirred solution of 143 mL of 1.4 M n-BuLi (0.20 mol) in 55 mL of dry THF, was added dropwise at room temperature under a nitrogen atmosphere 24.8 g (0.20 mol) of thioanisole. Upon completion of the addition, the yellow mixture began to reflux spontaneously. The mixture was stirred at room temperature for 3 hours. Upon addition of 21.84 g (0.20 mol) of chlorotrimethylsilane, the mixture again began to reflux spontaneously. After stirring at room temperature overnight, the mixture was quenched with 100 mL of 5% of HCl. The aqueous layer was separated, and the organic layer was dried over MgSO$_4$, filtered, and the solvent removed in vacuo from a water bath at 45° C. The crude product was distilled to give 19.22 g (49%) of the colorless sulfide, bp 84–°86° C./0.3 Torr; $^1$H NMR (CDCL$_3$) δ 0.17 (s, 9H, Si(CH$_3$)$_3$), 2.13 (s, 2H, CH$_2$S), 7.0–7.42 (m, 5H, phenyl).

EXAMPLE 32

Benzenesulfonyl Trimethylsilyl Methane. To a stirred mixture of 14.1 g (69.4 mmol) of 85% m-chloroperbenzoic acid in 300 mL of CH$_2$Cl$_2$ at 0° C. was added dropwise 6.82 g (34.7 mmol) of thiophenyl trimethylsilyl methane. The mixture was stirred at 0° C. for 3 hours and then at room temperature overnight. The mixture was extracted with three 75-mL portions of saturated NaHCO$_3$. The organic layer was dried over MgSO filtered, and the solvent removed in vacuo from a water bath at 45° C. The crude product was Kugelrohred at 115° C./0.1 Torr to give 6.83 g (86%) of the clear sulfone; $^1$H NMR (CDCl$_3$) δ 0.27 (s, 9H, Si(CH$_3$)$_3$), 2.8 (s, 2H, CH$_2$SO$_2$), 7.13–8.05 (m, 5H, phenyl).

EXAMPLE 33

2,2-Diphenyl-1-(phenylsulfonyl) Ethene. To a stirred solution of 2.0 g (8.76 mmol) of benzenesulfonyl trimethylsilyl methane in 20 mL of dry THF at 0° C., was added dropwise under a nitrogen atmosphere 6.25 mL of 1.4 M n-BuLi (8.75 mmol). The reddish-orange solution was stirred at 0° C. for 30 minutes. To the solution was added 1.60 g (8.78 mmol) of benzophenone. The solution was stirred at 0° C. for 2 hours, then at room temperature overnight. The reaction mixture was diluted with 50 mL of 5% HCl, and extracted with three 25-mL portions of water, dried over MgSO$_4$, filtered, and the solvent removed in vacuo from a water bath at 45° C. The crude product was recrystallized from 15% EtOAc/Skelly B to give 1.25 g (44%) of the slightly yellow sulfone, mp 111.0–°112.5° C.; $^1$H NMR (CDCl$_3$) δ 7.02 (s, 1H, vinyl), 7.12–7.72 (m, 15H, phenyl).

EXAMPLE 34

3,3-Diphenyl-2-(phenylsulfonyl)-2-propenyl Alcohol. To a stirred solution of 1.25 g (3.90 mmol) of 2,2-diphenyl-1-(phenylsulfonyl) ethene in 20 mL of dry THF at −78° C., was added dropwise under a nitrogen atmosphere 2.8 mL of 1.4M n-BuLi (3.90 mmol). The dark black solution was stirred at −78° C. for 30 minutes. Gaseous fomaldehyde, generated by heating paraformaldehyde at 170° C., was passed through a 5-mm tube into the reaction mixture with the aid of a slow stream of nitrogen at −78° C. for 30 minutes. The mixture was allowed to come to room temperature over a period of 30 minutes while continuing to pass formaldehyde through the reaction mixture until a pale yellow color was observed. The mixture was stirred overnight at room temperature. The mixture was quenched with 50 mL of 5% HCl, and extracted with three 25-mL portions of CH$_2$Cl$_2$. The organic layer was dried over MgSO$_4$, filtered, and the solvent removed in vacuo from a water bath at 45° C. The resulting crude oil was flash chromatographed on silica gel (230–400 mesh, 5×16-cm column) with 30% ether/Skelly B as eluant to give 0.47 g (34%) of the colorless alcohol. In a melting point capillary the compound does not melt but decomposes above 290° C. with blackening; IR (KBr) cm$^{-1}$ 3480, 3040, 1590, 1480, 1440, 1370, 1280, 1130, 1020, 960, 790, 730, 700, 680, 610; $^1$H NMR (CDCl$_3$) δ 3.47 (t, 1H, OH), 4.61 (d, 2H, CH$_2$O), 6.75–7.58 (m, 15H, phenyl).

Anal. Calcd for C$_{12}$H$_{18}$O$_3$S: C, 71.98; H, 5.18; S, 9.15. Found: C. 71.97; H, 5.22; S, 9.02.

EXAMPLE 35

3,3-Diphenyl-2-(phenylsulfonyl)-2-propenyl N-p-Chlorophenyl Carbamate. A solution of 0.35 g (1.0 mmol) of 3,3-diphenyl-2- (phenylsulfonyl) -2-propenyl alcohol and 0.15 g (1.0 mmol) of p-chlorophenyl isocyanate in 2 mL of benzene was refluxed for 18 hours. The solvent was removed in vacuo from a water bath at 45° C. Recrystallization from 95% EtOAc/EtOH gave 0.38 g (78%) of the colorless urethane. In a melting point capillary the compound does not melt but decomposes above 250° C.; IR (KBr) cm$^{-1}$ 3310, 1730, 1590, 1530, 1490, 1300, 1205, 1140, 1050, 825, 700, 680; $^1$NMR (CDCl$_3$) δ 5.13 (s, 2H, CH$_2$O), 6.80 (bs, 1H, NH), 6.91–7.58 (m, 19H, phenyl).

Anal. Calcd for C$_{28}$H$_{22}$ClNO$_4$S: C, 66.73; H, 4.40; N, 2.78. Found: C, 66.51; H, 4.44; N, 2.54.

EXAMPLE 36 cis-Phenyl β-Styryl Sulfide. To a solution of 150 mL of anhydrous ethanol maintained under nitrogen was added 3.45 g (0.15 mol) of sodium. The sodium dissolved within 25 minutes, and to the resulting sodium ethoxide solution was added 16.5 g (0.15 mol) of thiophenol. The solution was brought to reflux, and 15.0 g (0.15 mol) of phenylacetylene was added dropwise. The solution was refluxed overnight, cooled, and poured over crushed ice. The precipitate was filtered, dissolved in 100 mL of CH$_2$Cl$_2$, dried over MgSO$_4$, filtered, and the solvent removed in vacuo from a water bath at 45° C. The crude product was recrystallized from Skelly F to give 22.61 g (71%) of the sulfide, mp 43.0–°44.5° C.; $^1$NMR (CDCl$_3$) δ 6.51 (d, 2H, vinyl), 7.13–7.67 (m, 10H, phenyl).

EXAMPLE 37

(Z)-3-Phenyl-2-(thiophenyl)-2-propenyl Alcohol. To a solution of 1.0 g (4.7 mmol) of cis-phenyl β-styryl sulfide in 20 mL of dry THF at −78° C. was added dropwise under a nitrogen atmosphere 5.0 mL (7.0 mmol) of 1.4 M n-BuLi within 5 minutes. The light yellow solution was stirred at −78° C. for 30 minutes. Gaseous formaldehyde, generated by heating paraformaldehyde at 170° C., was passed through 5-mm tube into the reaction mixture with the aid of a slow steam of nitrogen at −78° C. for 3 hours. The mixture was allowed to come to room temperature over a period of 30 minutes and stirred overnight. The mixture was quenched with 30 mL of 5% HCl and extracted with three 25-mL portions of CH$_2$Cl$_2$. The organic layer was dried over MgSO$_4$, filtered, and the solvent removed in vacuo from a water bath at 45° C. to give a brown oil. The oil was flash chromatographed on silica gel (230–400 mesh, 4×18-cm packed column) with 20% EtOAc/Skelly B as eluant to give 0.50 g (45%) of the alcohol, mp 64.0–°65.0° C.; IR (KBr) cm$^{-1}$ 3240, 3140, 1580, 1470, 1090, 1070, 1010, 740, 695; $^1$H NMR (CDCl$_3$) δ 1.82 (broad, 1H, OH), 4.17 (d, 2H, CH$_2$O), 7.15–7.75 (m, 11H, phenyl and vinyl).

Anal. Calcd for C$_{15}$H$_{14}$OS: C, 74.35; H, 5.82; S, 13.23. Found: C, 74.35; H, 5.90; S, 13.18.

EXAMPLE 38

(Z)-3-Phenyl-2-(phenylsulfonyl)-2-propenyl Alcohol. A mixture of 0.47 g (1.94 mmol) of (Z)-3-phenyl-2-(thiophenyl)- 2-propenyl alcohol and 0.79 g (3.89 mmol) of 85% m-chloroperbenzoic acid in 10 mL of CH$_2$Cl$_2$ was stirred at room temperature overnight. The mixture was diluted with 40 mL of CH$_2$Cl$_2$ and extracted with three 50-mL portions of saturated NaHCO$_3$. The organic layer was dried over MgSO$_4$, filtered, and the solvent removed in vacuo from a water bath at 45° C. to give a clear oil. The oil was recrystallized from 20% EtOAc/Skelly B to give 0.27 g (51%) of the sulfone, mp 67.5–°69.0° C.; IR (KBr) cm$^{-1}$ 3280, 3180, 1445, 1300, 1150, 1080, 1025, 990, 750, 730, 650, 610; $^1$H NMR (CDCl$_3$) 2 85 (s, 1H, OH), 4.67 (s, 2H, CH$_2$O), 7.21–7.83 (m, 11H, phenyl and vinyl).

Anal. Calcd for C$_{15}$H$_{14}$O$_3$S: C, 65.67; H, 5.14; S, 11.69. Found: C, 65.45; H, 4.97; S, 11.82.

EXAMPLE 39

(Z)-3-Phenyl-2-(phenylsulfonyl)-2-propenyl N-p-Chlorophenyl Carbamate. A solution of 0.22 g (0.80 mmol) of (Z)-3-phenyl-2-(phenylsulfonyl)-2-propenyl alcohol and 0.12 g (0.78 mmol) of p-chlorophenyl isocyanate in 4 mL of benzene was refluxed overnight. The solvent was removed in vacuo from a water bath at 45° C. The crude product was recrystallized from 15% EtOAc/Skelly B to give 0.23 g (70%) of the urethane, mp 124.0–°125.0° C.; IR (KBr) cm$^{-1}$ 3320, 1740, 1590, 1525, 1300, 1210, 1120, 1050, 830, 740, 690; $^1$H NMR (CDCl$_3$) δ 5.23 (s, 2H, CH$_2$O), 7.05 (bs, 1H, NH), 7.22–7.83 (m, 15H, phenyl and vinyl).

Anal. Calcd for C$_{22}$H$_{18}$ClNO$_4$S: C, 61.75; H, 4.24; N, 3.27. Found: C, 61.70; H, 4.09; N, 3.21.

EXAMPLE 40

2-(Phenylsulfonyl)-2-propenyl chloroformate. Using the procedure from Example 5, 2-(phenylsulfonyl)-2-propenyl alcohol can be readily converted to 2-(phenylsulfonyl)-2-propenyl chloroformate.

EXAMPLE 41

2-Carbethoxy-2-propenyl chloroformate. Using the procedure from Example 5, 2-carbethoxy-2-propenyl alcohol can be readily converted to 2-carbethoxy-2-propenyl chloroformate.

EXAMPLE 42

2-(Phenylsulfonyl)-2-propenyl chloroformate. Using the procedure from Example 5,2-(phenylsulfonyl)-2-propenyl alcohol can be readily converted to 2-(phenylsulfonyl)-2propenyl chloroformate.

EXAMPLE 43

(E)-3-Phenyl-2-(phenylsulfonyl)-2-propenyl chloroformate. Using the procedure from Example 5, (E)-3-phenyl-2-(phenylsulfonyl)-2-propenyl alcohol can be readily converted to (E)-3-phenyl-2-(phenylsulfonyl)-2-propenyl chloroformate.

EXAMPLE 44

(Z)-3-Phenyl-2-(phenylsulfonyl)-2-propenyl chloroformate. Using the procedure from Example 5, (Z)-3-phenyl-2-(phenylsulfonyl)-2-propenyl alcohol can be readily converted to (Z)-3-phenyl-2- (phenylsulfonyl)-2-propenyl chloroformate.

EXAMPLE 45

3,3-Diphenyl-2-(phenylsulfonyl)-2-propenyl chloroformate. Using the procedure from Example 5, 3,3-diphenyl-2-(phenylsulfonyl)- 2-propenyl alcohol can be readily converted to 3,3-diphenyl-2-(phenylsulfonyl)-2-propenyl chloroformate.

EXAMPLE 46

Benzothiophene sulfone-2-methanol

Oxidation of 0.5 g of benzothiophene-2-methanol [F. F. Blicke and D. G. Sheets, *J. Am. Chem. Soc.*, 71, 2856 (1949)] with 2 eqs. of m-chloroperbenzoic acid in 20 mL methylene dichloride gave in 51% yield the sulfone alcohol, mp 112–°113° C.

Anal. Calcd for C$_9$H$_8$O$_3$S: C, 55.10; H, 4.08. Found: C, 54:81; H, 4.10.

The corresponding urethane derived from p-chlorophenyl isocyanate had mp 154–°56° C.

Anal. Calcd for C$_{16}$H$_{12}$ClNO$_4$S: C, 54.94; H, 3.43; N, 4.01; Cl, 10.16. Found: C, 54.87; H, 3.48; N, 3.94; Cl, 10.35.

EXAMPLE 47

Similarly, by using the procedures described herein and the appropriate starting materials, the following compounds are prepared:

3,3-dimethyl-2-(phenylsulfonyl)-2-propenyl alcohol 3,3-dimethyl-2-(phenylsulfonyl)-2-propenyl chloroformate Benzothiophenesulfone-2-methyl chloroformate.

EXAMPLE 48

Racemization Test

Preparation of Crude Methyl 2-(t-butylsulfonyl)-2-propenyloxycarbonyl-L-phenylalanyl-L-leucinate. A solution of 71.8 mg (0.185 mmol) of 2-(t-butylsulfonyl)-2-propenyloxy-carbonyl-L-phenylalanyl chloride and 33.6 mg of methyl L-leucinate hydrochloride in 5 mL of $CH_2Cl_2$ was stirred with 10 mL of saturated $NaHCO_3$ at room temperature for 2 hours. The aqueous layer was separated, and the organic layer washed with two 10-mL portions of saturated $NaHCO_3$, and two 100 mL portions of 5% HCl. The oranic layer was dried over $MgSO_4$, filtered, and the solvent removed in vacuo from a water bath at 45° C. to give 90 mg (98%) of the crude dipeptide as an oil.

HPLC Analysis. A mixture of 84 mg of the crude dipeptide and 2.11 g (10 eq) of piperazyl silica gel in 28 mL of $CH_2Cl_2$ was stirred at room temperature for 15 minutes. The silica gel was filtered, and washed with 15 mL of $CH_2Cl_2$. The solvent was removed by means of a slow stream of nitrogen. The deblocked dipeptide was dissolved in 5 mL of $CH_2Cl_2$, and to this solution was added 37 µL (1.9 eq) of benzoyl chloride, followed by 5 mL of saturated $NaHCO_3$. To the reaction mixture was added 170 µL or N-methylpiperazine, and the reaction mixture stirred at room temperature for 15 minutes, diluted with 15 mL of $CH_2Cl_2$, and the phases separated. The organic layer was washed with three 10-mL portions of 5% HCl, two 10-mL portions of saturated $NaHCO_3$, two 10-mL portions of water, dried over $MgSO_4$, filtered, and the solvent removed in vacuo from a water bath 45° C. to give 43 mg (69%) of the crude Bz-Phe-Leu-OMe, mp 153.0–°156.0° C. HPLC analysis was carried out on a Waters Radial Pak 10-um silica column (0.8×10 cm) using 3% 2-propanol in hexane as the mobile phase. Retention times (min) for the two diastereomeric benzoyl dipeptide esters were 15.3 (L,L) and 19.2 (D,L). Triplicate analysis showed <0.1% of the D,L diastereomer to be present.

GC Analysis. A mixture of 6 mg of the crude dipeptide and 0.302 g (20 eq) of piperazyl silica gel in 2 mL of $CH_2Cl_2$ was stirred at room temperature for 15 minutes. The silica gel was filtered, and washed with 4 mL of $CH_2Cl_2$. The solution was divided equally into two 2-mL Pierce Reactivials, and the solvent evaporated under a slow stream of nitrogen. The residue was dissolved in 1 mL of 6 N HCl, flushed with nitrogen, and heated at 110° C. for 24 hours. The solvent was evaporated under a slow stream of nitrogen. The residue was dissolved in 1 mL of 2N HCl in isopropanol, flushed with nitrogen, and heated at 110° C. for 1 hour. The solvent was evaporated under a slow stream of nitrogen. The residue was dissolved in 250 µL of ethyl acetate, and 50 µL of pentaflouropropionic anhydride was added. The solution was flushed with nitrogen, and heated at 110° C. for 10 minutes. The solvent was removed under a slow stream of nitrogen. The duplicate samples were dissolved in 100 µL of $CH_2Cl_2$. GC analysis was carried out on a Chrompack Chirasil-Val-L 25 m WCOT capillary column. Triplicate analyses on the two samples showed 0.83% of the D-phe enantiomer present. Analysis of a blank sample of phenylalanine showed 0.81% of the D-phe enantiomer. Subtracting the amount of the D-form found in the blank showed 0.02% of D-phe, which corresponds to 0.04% racemization for the full cycle preparation of acid chloride, coupling, and deblocking.

EXAMPLE 49

Deblocking of Bspoc-p-Chloroaniline via Benzylmercaptan. To a solution of 66,2 mg of Bspoc-Parachloroaniline in 0.4 mL of methanol-$d_4$ was added 100 mg of benzylmercaptan. Examination of the NMR spectrum before and after addition of the mercaptan showed that no reaction has occurred, To the solution was added 100 mg of N-ethyldiisopropylamine, Immediate NMR examination of the solution showed that complete deblocking of the urethane had occurred with the liberation of 100% of the free p-chloroaniline, When only N-ethyldiisopropylamine was added to a solution of the urethane (absence of mercaptan) NMR examination showed that no reaction occurred,

EXAMPLE 50

Leucine Enkephal

A. Standard Merrifield Method

A polyamide or polystyrene resin functionalized with leucine in the form of a trifluoroacetic acid-sensitive benzyl ester linkage is coupled with one equivalent of Bspoc-Phe-Cl in dimethyl formamide (DMF) for 3–5 min, Deblocking is effected by 10% piperidine or morpholine in DMF for 3–5 min, This is followed by treatment of the resultant peptide with one equivalent of Bspoc-Gly-Cl and subsequent deprotection, This is followed by treatment with a second equivalent of Bspoc-Gly-Cl. After deprotection the peptide is treated with an equivalent of Bspoc-Tyr(OBz)-Cl. Deprotection and removal from the resin support will furnish leucine enkaphalin,

B. Inverse Merrifield (two polymer) System

A general procedure for the preparation of a peptide by the use of active esters of the polymers is as follows:

1 equivalent of leucine having a C-terminal blocking group is introduced as the amine hydrochloride or trifluoroacetate to a suspension of 40% molar excess of the polymeric active ester of Bspoc-Phe to be coupled with the polymer in chloroform. 2 equivalents of triethylamine are added and the mixture shaken for 15–60 minutes. The polymer is washed with chloroform; the chloroform solution is then washed with water and with a cold solution of 10% $NaHSO_4$, and evaporated to yield the pure N-Bspoc peptide. The N-Bspoc protecting group is removed by polymeric piperazine in the usual manner and then the peptide is subjected to a new coupling cycle, the polymeric active ester Bspoc-Gly. After removal of the Bspoc group a second Bspoc-Gly group is coupled. This is followed by coupling with Bspoc-Tyr(OBz)-Cl. Following this procedure, the blocked enkephaline Bspoc-Tyr(OBz)-Gly-Gly-Phe-Leu-OBz may be prepared in an overall 90% or better yield.

The above preferred embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A compound of the formula

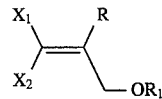

wherein $R_1$ is H or COZ;

$X_2$ is hydrogen, lower alkyl, aryl, aryl lower alkyl or polystyrene;

R and $X_1$ taken together with the carbon atoms to which they are attached form a bicyclic or tricyclic ring so that said compound has the formula:

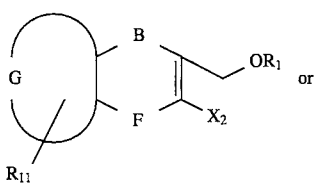 or

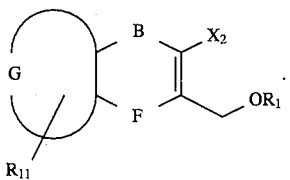

Z is an amino acid residue, a peptide residue or a leaving group;

B is a chemical bond, $CR_8CR_9$,

$SO_2$, SO or S;

F is

$SO_2$, SO, S or $CR_{12}R_{13}$;

Ring G is a mono or bicyclic fused ring system containing 5 to 10 ring carbon atoms and containing 1 or 2 ring heteroatoms selected from the group consisting of S, N and O, with the proviso that at least one of the heteroatoms is O or N; and $R_8, R_9, R_{11}, R_{12}, R_{13}$ are independently hydrogen or lower alkyl.

2. A compound of the formula:

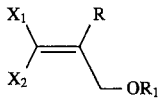

wherein R is an electron withdrawing group;

$R_1$ is H;

$X_1$ and $X_2$ are independently hydrogen, lower alkyl, aryl, aryl lower alkyl or polystyrene; or R and $X_1$ taken together with the carbon atoms to which they are attached form a monocyclic ring containing a sulfur ring atom or form a bicyclic or tricyclic ring so that said compound has the formula

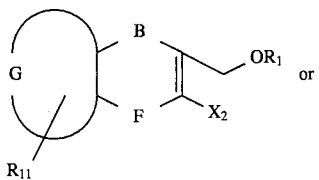 or

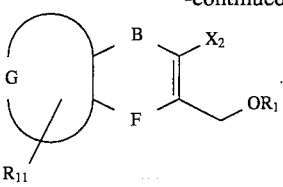

B is a chemical bond, $CR_8R_9$

$SO_2$, SO, or S;

F is a chemical bond, $CR_{12}R_{13}$, $SO_2$, S, SO or

Ring G is a mono or bicyclic fused ring system containing 5 to 10 ring carbon atoms and up to 2 ring heteroatoms wherein said ring heteroatoms are S, N or O, with the proviso that when ring G does not contain a ring heteroatom, then at least one of B or F is

$SO_2$, SO, or S; and $R_8, R_9, R_{11}, R_{12}$ and $R_{13}$ are independently hydrogen or lower alkyl.

3. A compound of the formula:

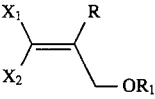

wherein $R_1$ is H or COZ;

R is an electron withdrawing group;

$X_1$ and $X_2$ are independently hydrogen, lower alkyl, aryl, aryl lower alkyl or polystyrene; or R and $X_1$ taken together with the carbon atoms to which they are attached form a monocyclic ring containing a sulfur ring atom or form a bicyclic or tricyclic ring so that said compound has the formula:

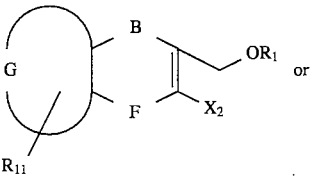 or

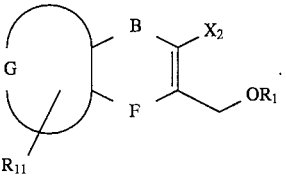

Z is an amino acid residue or peptide residue;

B is a chemical bond, $CR_8R_9$, $$\underset{O}{\overset{C,}{\|}}$$

$SO_2$, SO or S;

F is $$\underset{O}{\overset{C,}{\|}}$$

$SO_2$, SO, S or $CR_{12}R_{13}$;

Ring G is a mono or bicyclic fused ring system containing 5 to 10 ring carbon atoms and up to 2 ring heteroatoms wherein the heteroatoms are S, O, or N, with the proviso that when ring G does not contain a ring heteroatom, then at least one of B or F is $$\underset{O}{\overset{C,}{\|}}$$

$SO_2$, SO or S; and $R_8$, $R_9$, $R_{11}$, $R_{12}$ and $R_{13}$ are independently hydrogen or lower alkyl.

4. A compound of the formula:

wherein

R is 2-pyridyl or 4-pyridyl;

$R_1$ is H or COZ;

$X_1$ and $X_2$ are independently hydrogen, lower alkyl, aryl, aryl lower alkyl or polystyrene; and Z is an amino acid residue, a peptide residue or a leaving group.

5. The compound according to claim 2 wherein

R is an electron withdrawing group; and $X_1$ and $X_2$ are independently hydrogen, lower alkyl, aryl, aryl lower alkyl or polystyrene.

6. The compound according to claim 2 wherein

R and $X_1$ taken together with the carbon atoms to which they are attached form a bicyclic or tricyclic ring of the formula:

7. The compound according to claim 3 wherein

R is an electron withdrawing group;

$X_1$ and $X_2$ are independently hydrogen, lower alkyl, aryl, aryl lower alkyl or polystyrene;

$R_1$ is H or COZ; and

Z is an amino acid residue or peptide residue.

8. The compound according to claim 3 wherein R and $X_1$, taken together with the carbon atoms to which they are attached form a bicyclic or tricyclic ring so that said compound has the formula:

wherein $R_1$ is H or COZ; and

Z is an amino acid residue or peptide residue.

9. The compound according to claims 2, 3, 5 or 7, wherein R is $SO_2R_2$, $SOR_2$, $COOR_2$, $COR_2$, CHO, $CONR_2R_3$, CN, $CF_3$, $NO_2$, aryl or pyridyl, and $R_2$ and $R_3$ are independently lower alkyl, aryl aryl lower alkyl or heteroaryl 10. The compound according to claims 1, 3, 4, 7 or 8 wherein Z is an a-amino acid.

11. The compound according to claim 10 wherein Z is naturally occurring α-amino acid 12. The compound according to claim 10 wherein Z is alanine, arginine, asparagine, aspartic acid, cysteine, cystine, glutamic acid, glutamine, glycine, histidine, hydroxylysine, hydroxyproline, isoleucine, leucine, lysine, methionine, phenylalanine, proline, serine, threonine, tryptophan, tyrosine, valine, or penicillamine.

13. The compound according to claim 9 wherein R is $SO_2R_2$, $SOR_2$, $COOR_2$, $COR_2$, $CONR_2R_3$, aryl, 2-pyridyl or 4-pyridyl.

14. The compound according to claim 9 wherein R is SOhd $2C(CH_3)_3$, $SOC(CH_3)_3$, $SO_2C_6H_5$, $SOC_6H_5$, 2-pyridyl or 4-pyridyl.

15. The compound according to claim 1,1 3 or 4 wherein $R_1$ is COZ.

16. The compound according to claim 1 wherein Z is halo, CN, $SR_4$, $N_3$, OAr $R_4$ is lower-alkyl, aryl or aryl lower alkyl, wherein the alkyl or aryl groups are unsubstituted, or mono- or disubstituted with halides, $SO_2R_2$, $SOR_2$, $COOR_2$, CHO, $COR_2$, CN, $CF_3$, or $NO_2$, and $R_2$ is lower alkyl, aryl, lower alkyl or polystyrene.

17. The compound of claim 16 wherein Z is halo.
18. The compound of claim 17 wherein Z is Cl.
19. The compound according to claim 2, 3 or 4 wherein $X_1$ and $X_2$ are independently hydrogen, phenyl or lower alkyl having 1 to 4 carbon atoms.
20. The compound according to claim 3 wherein $R_1$ is COZ and R is an electron withdrawing group.
21. The compound according to claim 4 wherein Z is halo, CN, $SR_4$, SAr, $N_3$, OAr,

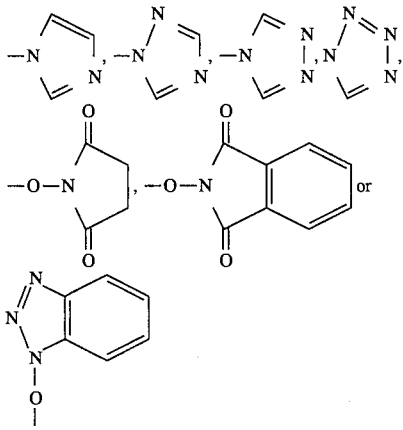

$R_4$ is a lower alkyl, aryl or aryl lower alkyl, wherein the alkyl or aryl groups are unsubstituted, or mono- di-substituted with halides, $SO_2R_2$, $SOR_2$, $COOR_2$, CHO, $COR_2$, CN, $CF_3$, or $NO_2$, and $R_2$ is lower alkyl, aryl, lower alkyl or polystyrene.
22. The compound of claim 21 wherein Z is halo.
23. The compound of claim 22 wherein Z is chloro.
24. The compound of claim 20 wherein Z is an amino acid residue.
25. The compound of claim 24 wherein Z is an a-amino acid residue.
26. The compound according to claim 1, 2 or 3 wherein ring G is a heterocyclic ring.
27. The compound according to claim 1, 2 or 3 wherein ring G is other than a heterocyclic ring.
28. The compound according to claim 1, 2 or 3 wherein at least one of B or F is $$\overset{C,}{\underset{O}{\|}}$$

$SO_2$, SO, or S.
29. The compound according to claim 1 or 3 wherein the compound has the formula:

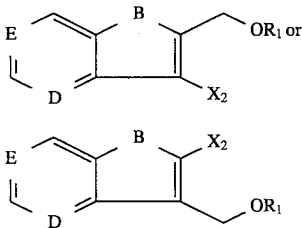

wherein $R_1$ is COZ;
B is $CR_8R_9$ or $SO_2$;
E and D are independently CH or N;
$R_8$ and $R_9$ are independently hydrogen or lower alkyl; provided that when B is $CR_8R_9$, then at least one of E or D is N;

$X_2$ is hydrogen, lower alkyl, aryl, aryl lower alkyl or polystyrene; and

Z is an amino acid residue or peptide residue.
30. The compound according to claim 29 wherein the compound has the formula:

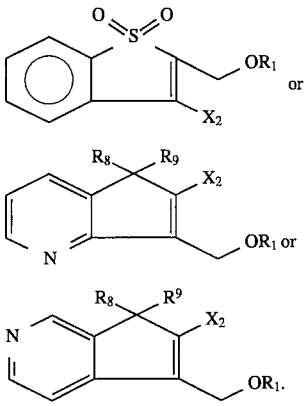

31. The compound according to claim 1 wherein the compound has the formula:

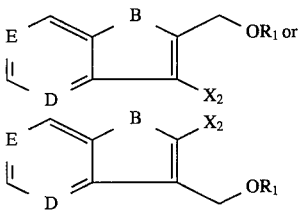

wherein B is $CR_8R_9$ or $SO_2$;
one of E and D is N and the other is CH or N;
$R_8$ and $R_9$ are independently hydrogen or lower alkyl and
Z is amino acid residue, peptide residue or leaving group.
32. The compound according to claim 2 wherein the compound has the formula:

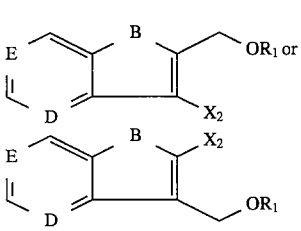

wherein $R_1$ is hydrogen;
B is $CR_8R_9$ or $SO_2$;
E and D are independently hydrogen or lower alkyl, provided that when B is $CR_8R_9$, then at least one of E or D is N; and
$X_2$ is hydrogen, lower alkyl, aryl, aryl lower alkyl or polystyrene.
33. The compound according to claim 31 which has the formula

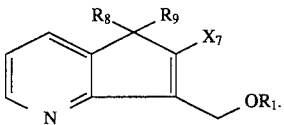

34. The compound according to claim 32 having the formula

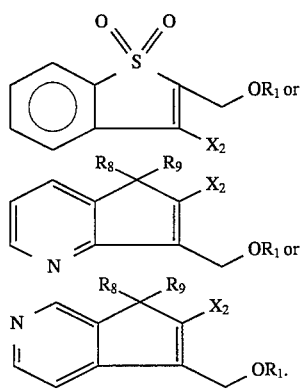

35. The compound according to claim 2 which is 2-(t-butylsulfonyl)- 2-propenyl alcohol.

36. The compound according to claim 2 which is benzothiophenesulfone-2-methanol.

37. The compound according to claim 2 which is
2-(phenylsulfonyl)-2-propenyl alcohol,
2-carboethoxy-2-propenyl alcohol,
2-(phenylsulfinyl)-2-propenyl alcohol;
(E)-3-phenyl-2-(phenylsulfonyl)-2-propenyl alcohol;
(Z)-3-phenyl-2-(phenylsulfonyl)-2 -propenyl alcohol;
3,3-dimethyl-2-(phenylsulfonyl)-2-propenyl alcohol, or
3,3-diphenyl-2-phenylsulonyl)-2-propenyl alcohol.

38. The compound according to claim 20 wherein R is $SO_2R_2$, $SOR_2$, $COOR_2$, $COR_4$, CHO, $CONR_2R_3$, CN, $CF_3$, $NO_2$, aryl, 2-pyridyl or 4-pyridyl, wherein $R_2$ and $R_3$ are independently lower alkyl, aryl, aryl lower alkyl or solid support.

39. The compound according to claim 38 wherein R is $SO_2R_2$, $SOR_2$, $CONR_4$, $COR_2$, $CONR_2R_3$, aryl, 2-pyridyl or 4-pyridyl.

40. The compound of claim 39 wherein R is $SO_2C(CH_3)_3$, $SOC(CH_3)_3$, $SO_2C_6H_5$, COOEt, 2-pyridyl or 4-pyridyl.

* * * * *

UNITED STATES PATENT AND TRADEMARK OFFICE
CERTIFICATE OF CORRECTION

PATENT NO. : 5,510,491
DATED : April 23, 1996
INVENTOR(S) : Louis A. Carpino, et al.

It is certified that error appears in the above-indentified patent and that said Letters Patent is hereby corrected as shown below:

Column 1, line 46: delete second occurrence of "the"

Column 4, line 25: after "hydrogen" delete --.--

Column 6, line 57: after "1:" insert the following:

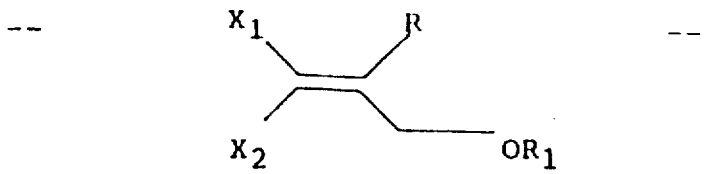

Column 8, line 67: under "halide" insert --6--

Column 13, line 5: "R1" should read --X1--

Column 13, line 33: "insolube" should read --insoluble--

Column 13, line 51: "CH3" should read --CMe3--

Column 16, line 66: "$^1$NMR" should read --1H NMR--

Column 17, line 17: after "(t-Butylsulfonyl" insert --)--

UNITED STATES PATENT AND TRADEMARK OFFICE
CERTIFICATE OF CORRECTION

PATENT NO. : 5,510,491
DATED : April 23, 1996
INVENTOR(S) : Louis A. Carpino, et al.

It is certified that error appears in the above-indentified patent and that said Letters Patent is hereby corrected as shown below:

Column 17, line 19: "retool" should read --mmol--

Column 17, line 29: "cm" should read --cm-1 --

Column 19, line 5: "of [" should read --of p--

Column 19, line 11: after "760;" delete --1--

Column 19, line 53: "2," should read --2- --

Column 20, line 20: "propenyoxcarbonyl" should read --propenyloxycarbonyl--

Column 20, line 59: " [x]D2 " should read --[x]23 --

Column 21, line 1: 1-butyl" should read --t-butyl--

Column 21, line 58: "$^1$HNMR" should read --1H NMR--

Column 22, line 20: "retool" should read --mmol--

Column 22, line 29: "bat.h" should read --bath--

Column 22, line 30: "1.01. g" should read --1.01 g--

Column 22, line 55: "1.70 H" should read --1.70--

Column 22, line 65: "t-Buty" should read --t-Butyl--

UNITED STATES PATENT AND TRADEMARK OFFICE
CERTIFICATE OF CORRECTION

PATENT NO. : 5,510,491

DATED : April 23, 1996

INVENTOR(S) : Louis A. Carpino, et al.

It is certified that error appears in the above-indentified patent and that said Letters Patent is hereby corrected as shown below:

Column 24, line 17: "7 23" should read --7.23--

Column 25, line 9: "5 14" should read --5.14--

Column 25, line 25: "tt," should read --H,--

Column 26, line 51: "$^1$NMR" should read --1H NMR--

Column 27, line 42: "2 85" should read --2.85--

Column 28, line 12: after "2" insert -- . --

Column 29, line 5: "oranic" should read --organic--

Column 29, line 59: "66,2" should read --66.2--

Column 29, line 63: after "occurred" delete "," and insert --.--

Column 29, line 64: after "isopropylamine" delete "," and insert --.--

Column 29, lines 66-67: after " chloroaniline" delete "," and insert --.--

Column 30, line 2: after "occurred" delete "," and insert --.--

Column 30, line 8: "Enkephal" should read --Enkephalin--

Column 30, lines 16 & 18: "min," should read --min.--

UNITED STATES PATENT AND TRADEMARK OFFICE
CERTIFICATE OF CORRECTION

PATENT NO. : 5,510,491
DATED : April 23, 1996
INVENTOR(S) : Louis A. Carpino, et al.

It is certified that error appears in the above-indentified patent and that said Letters Patent is hereby corrected as shown below:

Column 30, lines 19-20: after "deprotection" delete "," and insert --.--

Column 30, line 24: "enkaphalin," should read --enkephalin.--

Column 34, line 25, Claim 9: delete second occurrence of "aryl"

Column 34, line 25, Claim 9: after "heteroaryl" insert --.--

Column 34, line 27, Claim 10: "a-amino" should read -- $\delta$ -amino --

Column 34, line 29, Claim 11: after "acid" insert --.--

Column 34, line 39 Claim 14: "SOhd 2C" should read -- $SO_2C$ --

Column 34, line 40, Claim 15: "claim 1, 1 3" should read --claim 1, 3--

UNITED STATES PATENT AND TRADEMARK OFFICE
CERTIFICATE OF CORRECTION

PATENT NO. : 5,510,491
DATED : April 23, 1996
INVENTOR(S) : Louis A. Carpino, et al.

It is certified that error appears in the above-indentified patent and that said Letters Patent is hereby corrected as shown below:

Column 35, line 37, Claim 25: "a-amino" should read —$\delta$-amino—

Column 36, line 63, Claim 33: "X7" should read —X2—

Column 38, line 10, Claim 37: "phenylsulonyl)" should read —(phenylsulonyl)—

Signed and Sealed this

Fourteenth Day of October, 1997

Attest:

BRUCE LEHMAN

*Attesting Officer*  *Commissioner of Patents and Trademarks*